US010292572B2

United States Patent
Aoki

(10) Patent No.: US 10,292,572 B2
(45) Date of Patent: May 21, 2019

(54) BENDING DEVICE, CONTROL DEVICE, AND MEDICAL INSTRUMENT

(71) Applicant: Sharp Kabushiki Kaisha, Sakai, Osaka (JP)

(72) Inventor: Hitoshi Aoki, Sakai (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 178 days.

(21) Appl. No.: 15/301,986

(22) PCT Filed: Feb. 10, 2015

(86) PCT No.: PCT/JP2015/053676
§ 371 (c)(1),
(2) Date: Oct. 5, 2016

(87) PCT Pub. No.: WO2015/156022
PCT Pub. Date: Oct. 15, 2015

(65) Prior Publication Data
US 2017/0112358 A1    Apr. 27, 2017

(30) Foreign Application Priority Data

Apr. 10, 2014   (JP) ................. 2014-081368
May 30, 2014   (JP) ................. 2014-113332

(51) Int. Cl.
*A61B 1/00*       (2006.01)
*G02B 23/24*     (2006.01)
(Continued)

(52) U.S. Cl.
CPC ...... *A61B 1/00071* (2013.01); *A61B 1/00039* (2013.01); *A61B 1/00045* (2013.01);
(Continued)

(58) Field of Classification Search
CPC .... A61B 1/00071; A61B 1/0051–0053; A61B 1/015
(Continued)

(56) References Cited

U.S. PATENT DOCUMENTS 4,575,185 A * 3/1986 Wentzell ............... F22B 37/002
                                                             138/121
4,832,473 A * 5/1989 Ueda .................... A61B 1/0053
                                                             359/367
(Continued)

FOREIGN PATENT DOCUMENTS

JP      04-082527 A     3/1992
JP      06-125868 A     5/1994
(Continued)

OTHER PUBLICATIONS

Official Communication issued in International Patent Application No. PCT/JP2015/053676, dated Apr. 28, 2015.

*Primary Examiner* — Matthew J Kasztejna
(74) *Attorney, Agent, or Firm* — Keating & Bennett, LLP

(57) ABSTRACT

A bending device with which bending motions can be controlled with ease and good controllability includes a plurality of elastic tubes disposed inside an elastic tube. The elastic tubes each include an elastic tube body and a non-stretching body. The portion of the elastic tube body opposite the portion in which the non-stretching body is fixed inflates in a circumferential direction of the elastic tube body in response to increase in its internal pressure, causing the elastic tube to bend. The portion of the elastic tube body in which the non-stretching body is fixed is thicker than the remaining portion of the elastic tube body.

7 Claims, 19 Drawing Sheets

(51) Int. Cl.
*A61B 1/005* (2006.01)
*A61B 1/04* (2006.01)
*A61B 1/015* (2006.01)

(52) U.S. Cl.
CPC .......... *A61B 1/0052* (2013.01); *A61B 1/0055* (2013.01); *A61B 1/00147* (2013.01); *A61B 1/015* (2013.01); *A61B 1/04* (2013.01); *G02B 23/2476* (2013.01)

(58) Field of Classification Search
USPC .................. 600/115–116, 146, 152, 143
See application file for complete search history.

(56) References Cited

U.S. PATENT DOCUMENTS

| | | | | |
|---|---|---|---|---|
| 4,890,602 A * | 1/1990 | Hake | .................... | A61B 1/0053 600/144 |
| 4,962,751 A * | 10/1990 | Krauter | ................ | A61B 1/0053 600/152 |
| 5,018,436 A * | 5/1991 | Evangelista | ............ | F01B 19/00 600/152 |
| 5,018,506 A * | 5/1991 | Danna | .................. | A61B 1/0053 600/152 |
| 5,083,498 A * | 1/1992 | Sato | ...................... | F15B 15/125 73/731 |
| 5,179,934 A * | 1/1993 | Nagayoshi | ......... | A61B 1/00183 600/152 |
| 5,577,992 A * | 11/1996 | Chiba | .................. | A61B 1/0056 600/116 |
| 6,048,307 A * | 4/2000 | Grundl | ................ | A61B 1/0053 600/146 |
| 6,261,260 B1 * | 7/2001 | Maki | ...................... | A61L 29/04 428/35.5 |
| 6,478,772 B2 * | 11/2002 | Maki | ...................... | A61L 29/04 604/103.07 |
| 6,503,194 B2 * | 1/2003 | Pauker | ................. | A61B 1/0055 600/146 |
| 6,875,170 B2 * | 4/2005 | Francois | .............. | A61B 1/0053 600/141 |
| 6,899,674 B2 * | 5/2005 | Viebach | ............... | A61B 1/0008 600/115 |
| 7,762,948 B2 * | 7/2010 | Hirata | .................. | A61B 1/0051 600/139 |
| 9,186,049 B2 * | 11/2015 | Lee | ..................... | G02B 23/2476 |
| 2004/0097788 A1 * | 5/2004 | Mourlas | ............ | A61B 1/00082 600/116 |
| 2016/0249900 A1 * | 9/2016 | Aoki | .................... | A61M 25/0155 606/130 |
| 2017/0196436 A1 * | 7/2017 | Aoki | .................... | A61B 1/0057 |

FOREIGN PATENT DOCUMENTS

| | | |
|---|---|---|
| JP | 07-132115 A | 5/1995 |
| JP | 2000-271076 A | 10/2000 |
| WO | 2015/060034 A1 | 4/2015 |

* cited by examiner

2: ENDOSCOPE CAMERA
5: CONNECTING TUBE
10: ENDOSCOPE PART
20: CONTROL DEVICE
21: PISTON
22: SYRINGE
23: AIR PRESSURE SENSOR
24: PISTON DRIVING UNIT
25: MICROPHONE
26: PRESSURIZATION CONTROL UNIT
28: PRESSURIZING VALVE DRIVING UNIT
30: ARTICULATED BENDING PORTION
31: BENDING PORTION
32: NON-BENDING PORTION
36: PRESSURIZING VALVE
100: ENDOSCOPE DEVICE 3a, 3b, 3c, 3d: NON-INFLATING TUBES
4: NON-STRETCHING BODY
11: ELASTIC TUBE BODY
13: FIXING PORTION
32: NON-BENDING PORTION
33: RIGID TUBE
34: NON-INFLATING BODY

BENDING DEVICE, CONTROL DEVICE, AND MEDICAL INSTRUMENT

TECHNICAL FIELD

The present invention relates to a bending device, a control device, and a medical instrument. More particularly, the present invention relates to a medical instrument as an endoscope device for taking images of an affected area during a medical procedure or an operation on a patient, for example, an endoscope device suited for use in an endoscopic surgery using a rigid endoscope such as a laparoscope or a thoracoscope, in particular a single-port laparoscopic surgery. The present invention also relates to a medical instrument equipped with a catheter, a laser scalpel, or an electric scalpel, for example, as a medical device.

BACKGROUND ART

An endoscopic surgery using a rigid endoscope such as a laparoscope or a thoracoscope is a low-invasive operation for performing a test or treatment procedure without opening the patient's abdomen. In an endoscopic surgery, a medical device such as forceps and an endoscope are separately introduced into a body cavity of the patient. The operator then sets the distal end portion of the medical device inserted into the body cavity such that it is imaged in the observation field of view of the endoscope and conducts the procedure tasks while observing the state of the area being treated with the medical device through the endoscope. In an endoscopic surgery, medical devices and an endoscope are introduced into a body cavity through four or five pipes (tubular members, so-called trocars) inserted into the body wall (for example, abdominal wall) such as in the patient's abdomen.

When cutting open or suturing an organ, the operator inserts the endoscope and medical devices into separate trocars. Trocars are disposed in advance at positions suited for the operation to be performed, and for reducing the patient's burden, they are never changed to different positions once they are set. Thus, the manipulation of the endoscope and medical devices is limited by the positions of trocars and such devices can interfere with each other depending on the circumstance of the operation.

A single-port laparoscopic surgery is a method in which a single small hole of about 15 mm is made in the patient's navel through which forceps (a medical device) and an endoscope camera are inserted for resecting and removing the gallbladder, for example. In a single-port laparoscopic surgery, a surgeon (a camera assistant) manipulates the endoscope camera to capture the image of the inside of the patient's body, which is displayed on a camera monitor outside the body. A surgeon (the operator) different from the camera assistant conducts the operation while watching the camera monitor by manipulating two pairs of forceps respectively held in his right and left hands. The endoscope camera captures the affected area of the patient from above the forceps.

Because a single-port laparoscopic surgery leaves a scar only in the navel, it adds to the advantages of endoscopic surgeries over open procedures as follows:

(1) Being cosmetically favorable due to a less noticeable scar.

(2) Less pain after the operation.

(3) Shorter hospital stay (two or three days) than conventional operation methods because of quick recovery, thus helping reducing health care costs.

(4) Capable of being safely performed on physically weak patients (elderly people) because of low burden on the body.

On the other hand, the conventional single-port laparoscopic surgeries have the following problems:

(1) Contact and interference between persons and surgery devices outside the patient's body.

(2) Contact between the operator and the camera assistant.

(3) Contact between forceps and the endoscope camera.

In order to overcome these problems of endoscopic and single-port laparoscopic surgeries, the distal end portion of an endoscope device is required to have a curvable structure for taking images of the area being treated in the abdominal cavity. Such a curving structure is typically formed from wires for manipulating multiple joints by pulling them. Another type of known curving structure produces a bending motion by supplying fluid to its interior and inflating an elastic pressurizing chamber with the pressure of the fluid (PTLs 1 and 2).

PTL 1 discloses a configuration of a flexible tube having a curving portion including three elastic pressurizing chambers per joint, where the pressurizing chambers and multiple pressurizing tubes as many as the number of pressurizing chambers are disposed on the outer periphery of the flexible tube. PTL 1 discloses embodiments with mesh tubes used as pressurizing tubes for prevention of stretching or fibrous material wrapped around the pressurizing tubes.

PTL 2, for example, discloses a configuration of a flexible tube having a curving portion with three elastic pressurizing chambers per joint, where the pressurizing chambers and multiple non-stretching pressurizing tubes as many as the number of pressurizing chambers are disposed in the wall of the flexible tube.

CITATION LIST

Patent Literature

PTL 1: Japanese Unexamined Patent Application Publication No. 6-125868 (published on May 10, 1994)

PTL 2: Japanese Unexamined Patent Application Publication No. 2000-271076 (published on Oct. 3, 2000)

SUMMARY OF INVENTION

Technical Problem

While the flexible tube of PTL 1 and the endoscope device of PTL 2 cause curving of the curving portion by pressurizing and inflating pressurizing tubes, the curving angle of the curving portion is small relative to the amount of inflation of the pressurizing tubes because the pressurizing tubes inflate uniformly in the entire circumferential direction. Thus, a large pressure needs to be applied to the pressurizing tubes so that the flexible tube curves at a desired angle, making curving not easy to control.

The configuration disclosed in PTL 1 requires at least three pressurizing tubes per joint, and the number of pressurizing tubes increases proportionately to increase of the joints. Thus, when there are many joints, it is difficult to dispose the pressurizing tubes on the outer periphery of the flexible tube, making it difficult to increase the joints over a certain number. A further problem of this configuration is that increase in pressurizing tubes that are not pressurized and pressurizing tubes that are pressurized and stiffened in a linear shape place burden on bending motions, and normal bending motions cannot be effected because pressurizing tubes that are stiffened in a case where the number of joints is large are at a higher ratio to pressurizing tubes that are stiffened in a case where the number of joints is small.

The configuration disclosed in PTL 2 requires at least three pressurizing chambers and pressurizing tubes for feeding to joints on the distal end side per joint; the pressurizing chambers and pressurizing tubes increase proportionately to increase in the number of joints, and thus they are difficult to dispose in the wall of the flexible tube when there are many joints. Also, an increased number of non-stretching pressurizing tubes as components place burden on bending motions, causing the problems of interfering with bending motions or preventing a bend from occurring.

The present invention has been made in view of these challenges and an object thereof is to provide a bending device with which bending motions can be controlled with ease and good controllability.

Furthermore, the present invention solves the aforementioned problems encountered in conventional endoscopic or single-port laparoscopic surgeries, for example, by providing a safe device capable of conducting complicated and free bending motions with good controllability despite a simple structure by employing a novel structure that uses elastic tubes for curving motions at the distal end portion of a medical instrument such as an endoscope device, and also enabling automatic manipulation of curving motions through a control device.

Solution to Problem

In order to solve the aforementioned problems, a bending device according to one aspect of the present invention is a bending device which allows attachment of a medical device at a distal end, including a tubular member having a hollow structure, and a plurality of elastic tubes disposed inside the tubular member, characterized in that the elastic tubes each include an elastic tube body which is sealed at a distal end portion and has an elongated, hollow cylindrical shape, and a non-stretching body for suppressing inflation of the elastic tube body; the non-stretching body is fixed to the elastic tube body; a portion of the elastic tube body in which the non-stretching body is fixed is thicker than a remaining portion of the elastic tube body; and a portion of the elastic tube body opposite the portion in which the non-stretching body is fixed inflates in a circumferential direction of the elastic tube body in response to increase in an internal pressure, causing the tubular member to bend.

Advantageous Effects of Invention

According to one aspect, the present invention can provide a bending device with which bending motions can be controlled with ease and good controllability.

The present invention employs a structure in which fluid (for example, air) is contained in soft elastic tubes and the elastic tubes are made to curve utilizing the pressure of the fluid. Thus, even if the articulated bending device formed from such elastic tubes contacts the treated area (for example, an organ), the individual elastic tubes deform to absorb the shock associated with the contact, causing no damage to the treated area to ensure safety. Additionally, due to the simple structure of the individual elastic tubes, they can be inexpensively manufactured and easily disposed of after use (that is, are disposable), thus facilitating maintenance of cleanliness.

Also, because it uses air pressure, for example, as the force for curving tubes, it offers the advantage of not contaminating the treated area even if air leaks from an elastic tube. Moreover, because it uses non-inflated elastic tubes as narrow tubes for insertion into the treated area (the body) during a medical procedure, the distal end portion of a medical instrument (for example, an endoscope) can be made thin. Further, since the distal end portion of the medical instrument can be automatically manipulated, there is no need for a surgeon (a camera assistant) to manipulate the distal end portion of the medical instrument and thus manipulation by such a surgeon would not interfere with the medical procedure (operation) conducted by a surgeon (the operator).

As shown above, the present invention is highly convenient for medical settings as it employs a simple structure which is easy and inexpensive to manufacture yet is disposable and non-invasive to the human body, being expected to gain wide use in medical settings.

BRIEF DESCRIPTION OF DRAWINGS

FIG. 6(a) is a cross-sectional view showing an example of a pressurizing portion, FIG. 6(b) is a cross-sectional view of a pressurizing valve, and FIGS. 6(c) to 6(f) show examples of the arrangement position of the opening in the pressurizing valve.

FIG. 7(a) illustrates a non-bent state and FIG. 7(b) illustrates a bent state.

FIG. 10(a) is a cross-sectional view of the distal end portion, FIGS. 10(b) and 10(c) are cross-sectional views showing an example of the configuration of the middle and proximal end portions, FIGS. 10(d) and 10(e) are cross-sectional views showing another example of the configuration of the middle and proximal end portions.

FIG. 11(a) is a cross-sectional view of the distal end portion and FIGS. 11(b) and 11(c) are cross-sectional views showing an example of the configuration of the middle and proximal end portions.

FIGS. 18(a) and 18(b) are graphs for a case of a single elastic tube alone, and FIGS. 18(c) and 18(d) are graphs for a case with another elastic tube on its periphery.

FIG. 19(a) is a state in which tube A is pressurized but not inflated yet, FIG. 19(b) is a state in which tube A inflates and its pressure starts to be applied to the peripheral tube, FIG. 19(c) is a state in which the peripheral tube also starts inflating, and FIG. 19(d) is a state in which the inflation of the peripheral tube has advanced.

DESCRIPTION OF EMBODIMENTS

[Embodiment 1]

Embodiments of the present invention will be described below in detail based on FIGS. 1 to 6, 18, and 19.

The bending device according to the present invention is a medical instrument to which a medical device can be attached at the distal end. While an articulated bending portion 30 having multiple deformable bending portions 31 (joints) will be described as an example of the bending device according to the present invention, the bending device according to the present invention includes a bending device with a single joint as well.

(Overview of the Medical Instrument)

Figure 1:
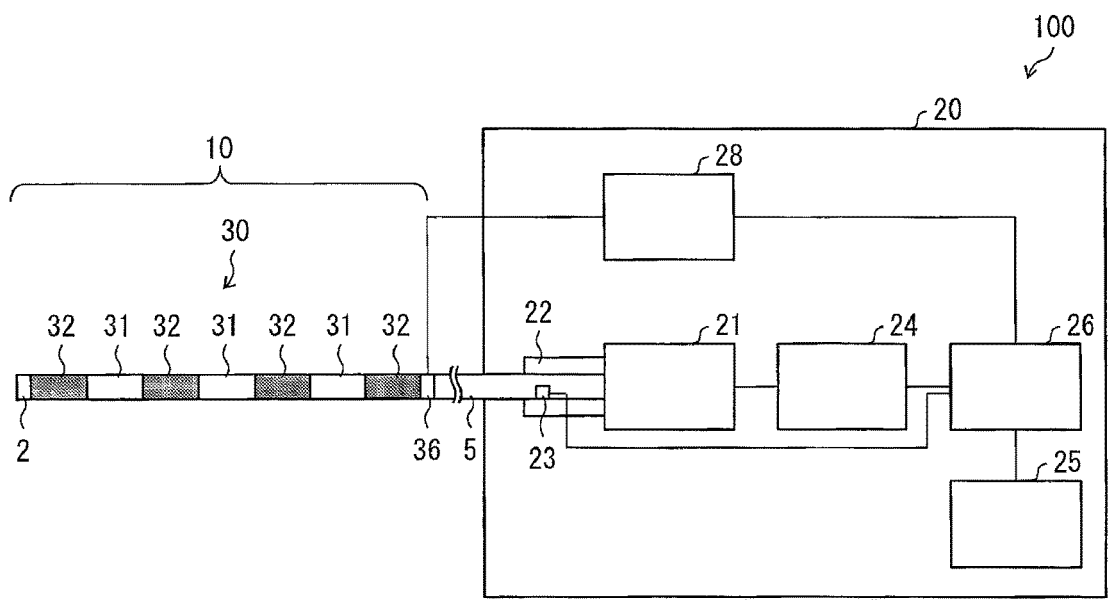
FIG. 1 shows the configuration of a medical instrument (an endoscope device) including the articulated bending portion according to Embodiment 1 of the present invention.

FIG. 1 shows the configuration of an endoscope device as an example of a medical instrument including elastic tubes according to an embodiment of the present invention. In FIG. 1, an endoscope device 100 (a medical instrument) includes an endoscope part (medical instrument part) 10 and a control device 20. The control device 20 drives and controls the endoscope part 10. The control device 20 will be described in detail later.

Figure 2:
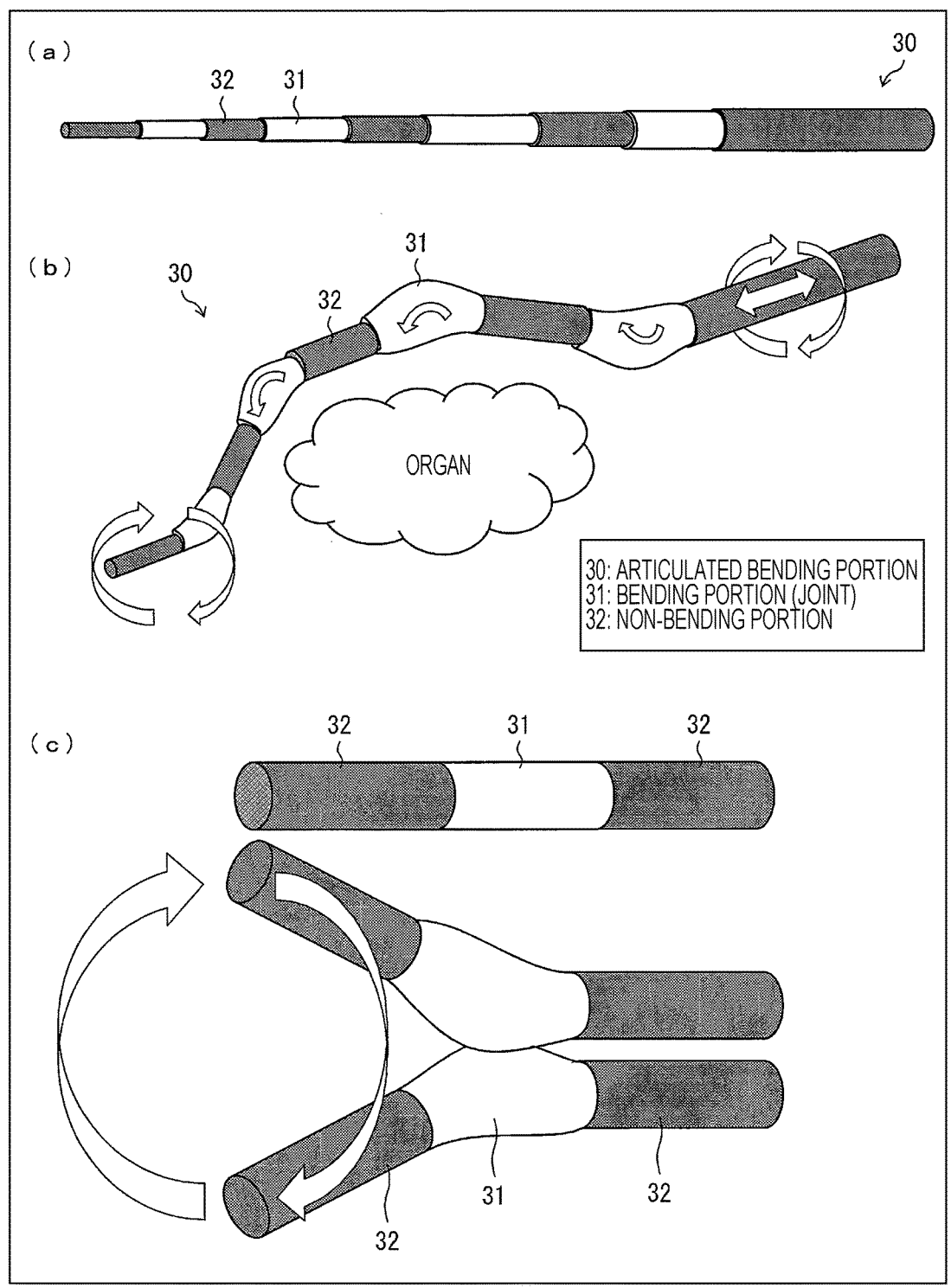
FIGS. 2(a) to 2(c) are perspective views generally showing the articulated bending portion in Embodiment 1.
Figure 3:
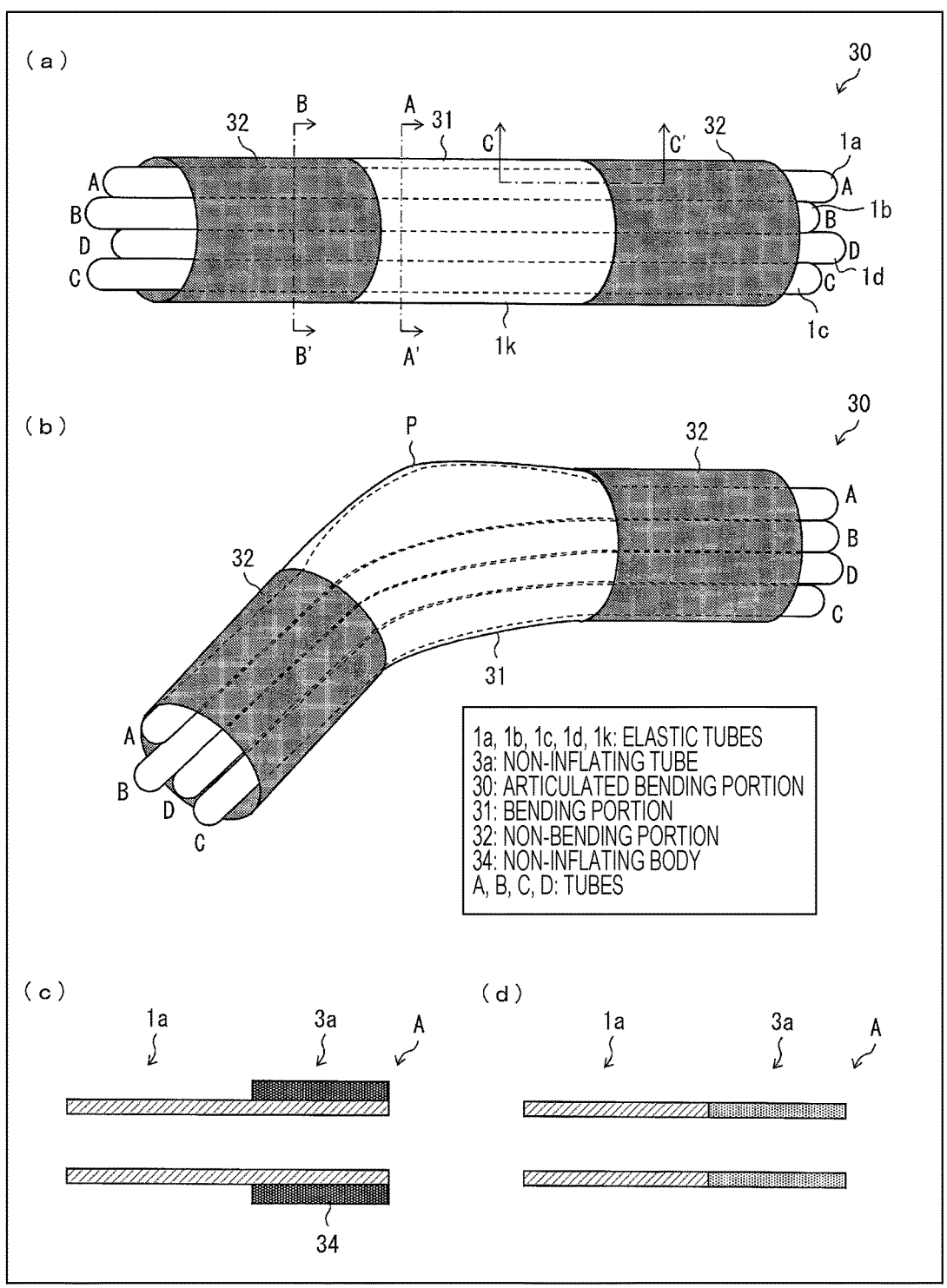
FIG. 3 shows an example of the internal structure of the articulated bending portion in Embodiment 1, FIGS. 3(a) and 3(b) being perspective views, and FIGS. 3(c) and 3(d) being cross-sectional views.

As shown in FIGS. 2 and 3, the endoscope part 10 is composed of an articulated bending portion 30 consisting of multiple bending portions (joints) 31 formed from multiple inflatable elastic tubes 1, which have an elongated, hollow cylindrical shape and contain air (gas) W, and multiple non-bending portions 32, an endoscope camera (a medical device) 2 mounted at the distal end of the articulated bending portion 30, and non-inflating tubes (not shown) connected between the articulated bending portion 30 and a pressurizing valve.

Figure 4:
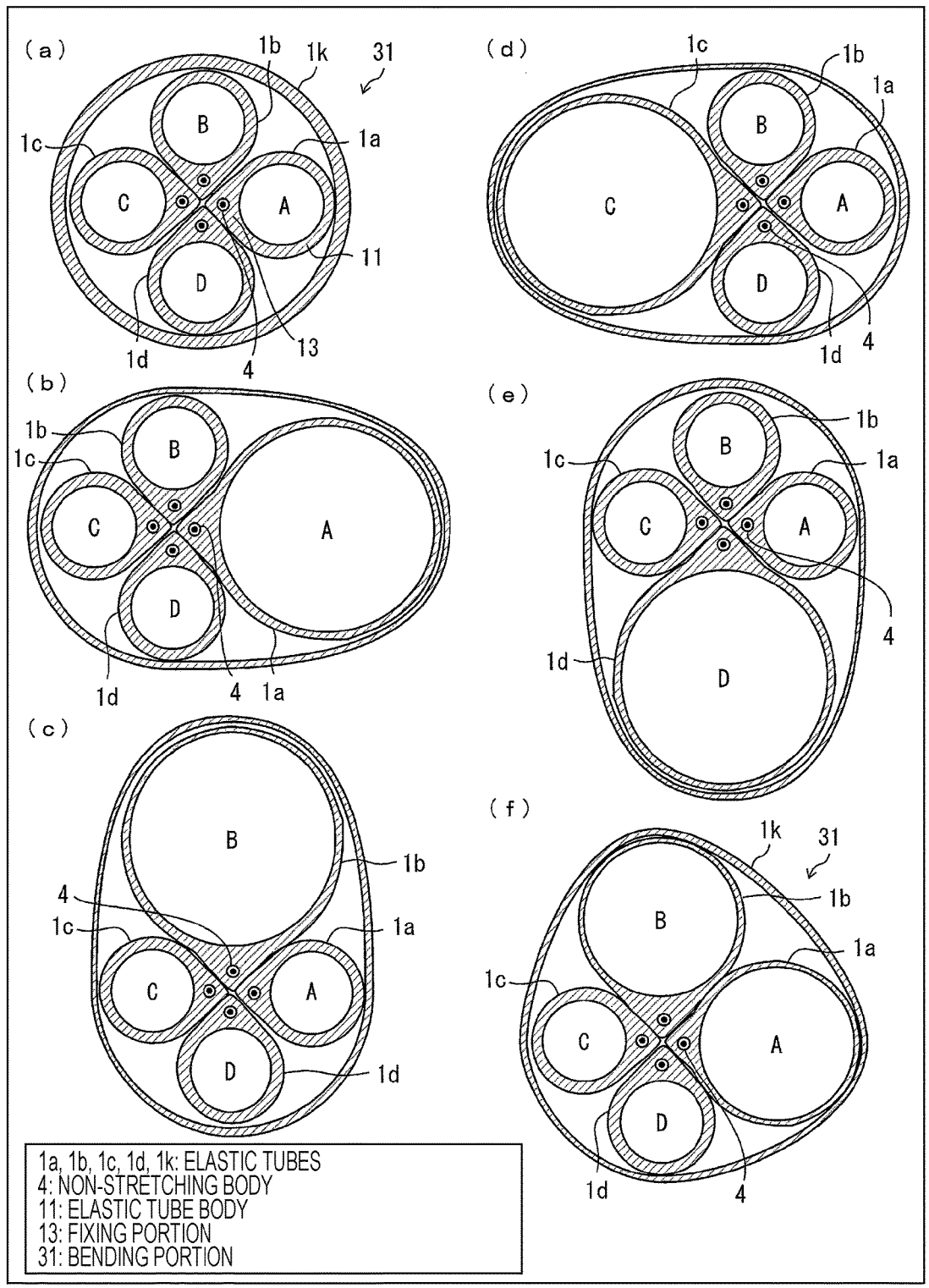
FIGS. 4(a) to 4(f) are cross-sectional views showing an example of the internal structure of a bending portion of the articulated bending portion.
Figure 5:
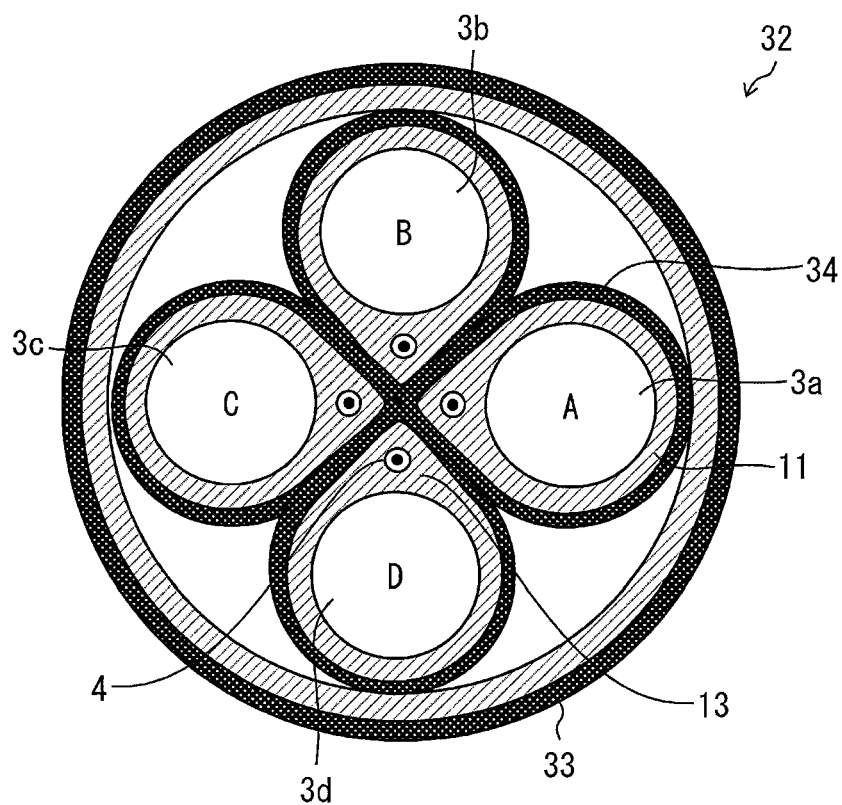
FIG. 5 is a cross-sectional view showing an example of the internal structure of a non-bending portion of the articulated bending portion.

FIG. 4(a) is a cross-sectional view seen from the arrow in line A-A' in FIG. 3(a). FIG. 5 is a cross-sectional view seen from the arrow in line B-B' in FIG. 3(a).

As illustrated in FIGS. 3 and 4(a) for example, the bending portion 31 is composed of four elastic tubes 1a, 1b, 1c, 1d, in each of which a flexible non-stretching body 4 fixed in the long-axis direction is embedded, and an elastic tube 1k (a tubular member) that has a hollow structure and accommodates the elastic tubes 1a to 1d inside.

The non-bending portion 32 is composed of four non-inflating tubes 3a to 3d having the non-inflating bodies 34 around the elastic tubes 1a to 1d, and a rigid tube 33 containing the non-inflating tubes 3a to 3d inside, as illustrated in FIG. 5, for example. (As the hollow portion of the elastic tube 1a communicates with that of the non-inflating tube 3a, they are collectively termed as tube A. The same applies to tube B and so on.)

(Overview of the Articulated Bending Portion)

The elastic tubes 1a to 1d forming the articulated bending portion each have a structure in which the flexible non-stretching body 4 fixed in the long-axis direction is embedded between the inner circumferential surface and the outer circumferential surface.

FIGS. 4(b) to 4(e) respectively show the elastic tubes 1a to 1d of the bending portion (joint) 31 in an inflated state due to the pressure of air W (fluid) injected from the control device 20. By thus pressurizing the individual elastic tubes, bends in four directions can be produced. Bend in an intermediate direction is also possible by selecting arbitrary two elastic tubes as shown in FIG. 4(f). Further, a rotational motion such as shown in FIG. 2(c) can also be produced by sequentially pressurizing the elastic tubes while adjusting the pressure.

FIG. 5 shows the cross-sectional structure of the non-bending portion 32. The non-inflating tubes 3a to 3d are structured by wrapping the non-inflating body 34 around the elastic tubes 1a to 1d. The outermost circumference of the non-bending portion 32 is formed of the rigid tube 33. Thus, the non-inflating tubes 3a to 3d do not inflate when the elastic tubes 1a to 1d are pressurized, so that the bending portions 31 can be bent without bending the non-bending portions 32.

The elastic tubes inside the non-inflating tubes 3a to 3d in the rigid tube 33 are not required to have the non-stretching body 4 in terms of their function because they already have the non-inflating bodies 34 around them as shown in FIG. 5. For convenience of fabrication, however, forming the non-stretching body 4 as an integral part in advance irrespective of bending or non-bending portions allows formation of bending portions 31 and non-bending portions 32 only with the presence or absence of the non-inflating body 34 and the rigid tube 33, and also increases the freedom of design. For this reason, all the elastic tubes in drawings are depicted in an exemplary structure including the non-stretching body 4.

(Overview of the Elastic Tube)

As shown in FIGS. 4(a) and 5, the elastic tube 1 includes an elastic tube body 11, the non-stretching body 4, and a fixing portion 13 for fixing the non-stretching body 4. The elastic tube body 11 is a primary component forming the elastic tube 1. The fixing portion 13 is provided in the long-axis direction of the elastic tube 1 and can fix the non-stretching body 4. While the non-stretching body 4 may be configured to be fixed to the outer or inner circumferential surface of the elastic tube by means of the fixing portion 13, it will be described here by taking an example where it is fixed being embedded between the outer and inner circumferential surfaces of the elastic tube body 11 (a thick wall portion) as shown in FIG. 4(a). The articulated bending portion 30 is formed of a set of four such elastic tubes 1 as a basic structure, and its tip on the side on which the endoscope camera 2 is mounted is sealed. A mounting portion for mounting the endoscope camera 2 is formed at the sealed tip of the articulated bending portion 30, enabling attachment of a medical device to the articulated bending portion 30. The medical device to be attached to the mounting portion is not limited to the endoscope camera 2 but may be a catheter, a laser scalpel, or an electric scalpel, for example. The mounting portion and the fixing portion 13 are parts of the elastic tube 1 and made of the same material as the elastic tube 1.

If the elastic tube body 11 has a structure with a uniform thickness for example, the portion in which the non-stretching body 4 is fixed particularly receives stress during pressurization and thus is easier to deteriorate locally. In a structure combining four elastic tubes 1 as shown in FIG. 4(a), a space is created between the tubes and the space can be utilized to make the thickness of the elastic tube body 11 in the portion where the non-stretching body 4 is fixed larger than the remaining portion, in which no non-stretching body 4 is fixed. This improves the durability of the fixing portion 13 and also increases the non-stretchability, providing the effect of achieving stable bending motions with no hysteresis to pressurization.

(Pressurization of Elastic Tubes)

Figure 6:
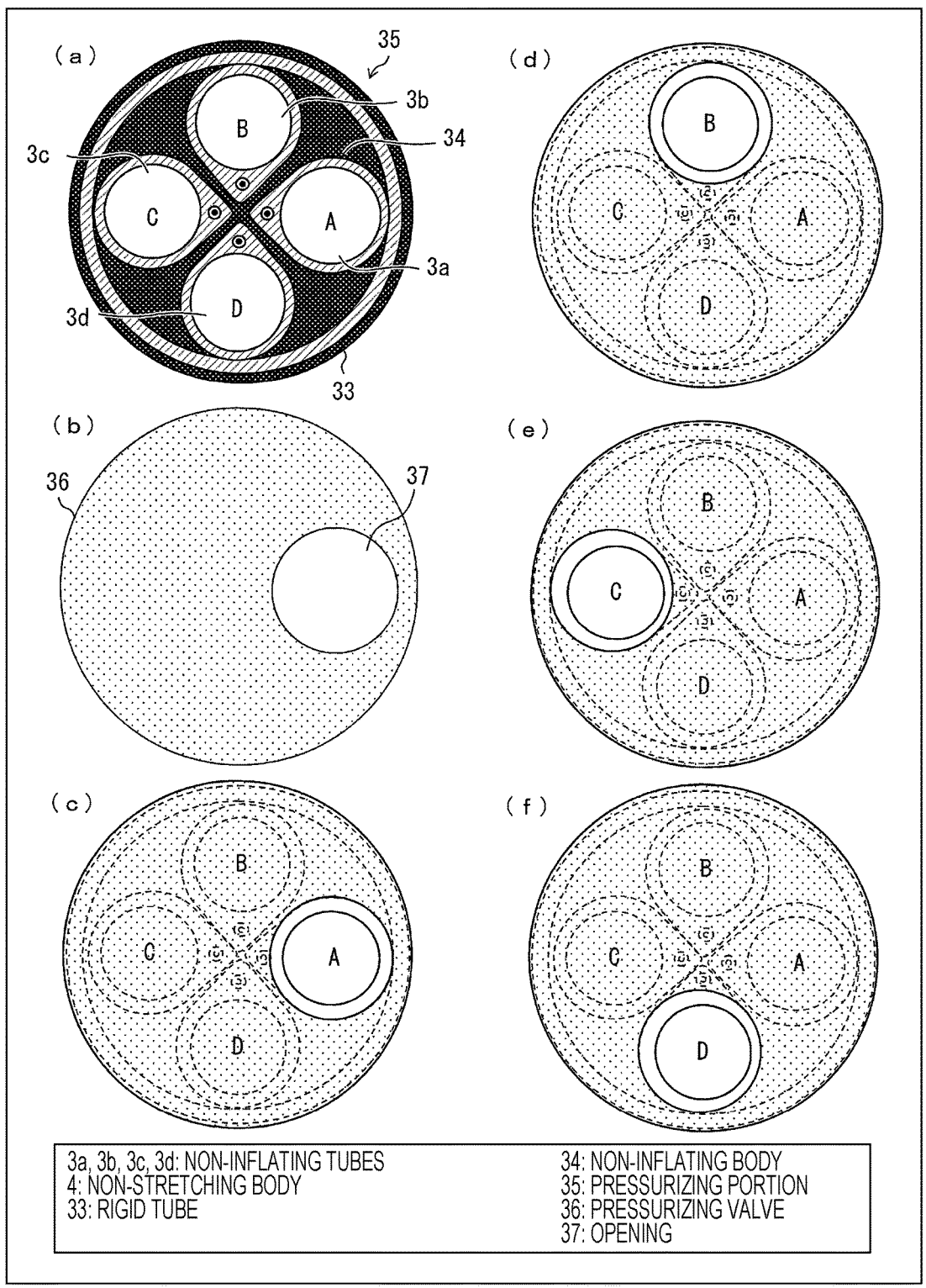
FIG. 6 shows cross-sectional views of the articulated bending portion, where

Turning now to FIG. 6, an exemplary configuration of a pressurizing portion 35 for the elastic tubes 1 will be described. FIG. 6(a) shows an example for a relatively simple configuration with four elastic tubes 1, showing the cross section of the non-bending portion 32 at the proximal end of the articulated bending portion 30.

At the proximal end of the articulated bending portion 30, which refers to the end on the side of the control device 20, a pressurizing portion 35 for pressurizing the elastic tubes 1 is provided. As shown in FIG. 6(a), the proximal end is structured such that only the insides of the non-inflating tubes 3a to 3d are open and the remaining portion is sealed. In practice, a medical device such as an endoscope camera is attached to the distal end and thus cables for power supply and signals or the like are drawn from the side of the sealed portion, for example, though they are omitted in this drawing.

FIG. 6(b) shows an exemplary structure of a pressurizing valve 36, and FIGS. 6(c) to 6(f) shows configurations in which the pressurizing valve 36 is disposed on the pressurizing portion 35.

By setting the pressurizing valve 36 shown in FIG. 6(b) on the pressurizing portion 35 and applying rotational movement to the pressurizing valve 36 as illustrated in FIGS. 6(c) to 6(f), pressure can be sequentially applied so as to pressurize only tube A, tubes A and B, only tube B, tubes B and C, only tube C, tubes C and D, tube D and so on. In response to the rotation of the pressurizing valve 36, rotational movement of the endoscope camera 2 attached on the distal end can be produced as illustrated in FIG. 2(c).

This will be described more specifically. The pressurizing valve 36 has an opening 37. Tubes A, B, C, and D are supplied with and pressurized by air W from the control device 20, to be discussed later, through the opening 37. The pressurizing valve 36 rotates in response to control by the control device 20, so that the position of the opening 37 can be changed. A tube to be pressurized can be thereby selected and air W can be supplied to that tube.

Employing such a configuration can provide a straightforward and intuitively operable control mechanism in which the distal end portion rotates in synchronization with the rotation of the pressurizing valve.

Although the pressurizing valve 36 is described here as being connected to the proximal end of the articulated bending portion 30, this is not limitative and the pressurizing valve 36 may also be provided in a middle of a non-inflating tube or the connecting tube 5 or a junction between them on the way of connection to the pressurization control device 20. Because an actuating mechanism for the valve is to be provided, the pressurizing valve 36 is desirably disposed in a proximal end portion close to the control device 20 as much as possible so that it does not interfere with a surgical procedure.

In addition, pressurizing portions may be provided at two or more locations, including a pressurizing portion for pressurizing the four tubes that drive the distal end portion and a pressurizing portion for pressurizing the four tubes that drive the middle to proximal end portions. This will be described in greater detail later as Embodiment 6.

Alternatively, instead of relying on the pressurizing valve structure described above, separate pressurization mechanisms may be provided for the respective tubes to independently control them so that fine position control allowing control to a desired position is performed in addition to rotation.

(Inflation of Elastic Tubes)

Using now FIGS. 3, 4, 18, and 19, inflation of the elastic tube 1 will be described in greater detail. FIG. 3(a) is a perspective view showing the primary components of the articulated bending portion 30, which constitutes the endoscope part 10 of the endoscope device 100 in FIG. 1. FIG. 4(a) is a cross-sectional view of the bending portion 31 of the endoscope part 10 in FIG. 3(a) as seen from the arrow in line A-A'. The elastic tube 1 shown in FIG. 4 is made of a silicone (polydimethylsiloxane with a reinforcing agent such as silicon oxide added) tube having an outer diameter of 2 mm, an inner diameter of 1 mm, and a length of 5 mm, for example. The elastic tube 1 inflates and deflates with the pressure of air W injected into the elastic tube 1 from the control device 20 (see FIG. 1). When the air W contained in the elastic tube 1 is at the atmospheric pressure (1 atm), the articulated bending portion 30, which is formed from such elastic tubes 1 as primary components, takes a linear shape as illustrated in FIG. 3(a). By increasing the pressure of air W contained in the elastic tube 1a (tube A), the elastic tube 1a (tube A) inflates in the bending portions 31 as shown in FIG. 3(b).

An LED lamp (not shown) for illumination may be attached adjacent to the mounting portion on which the endoscope camera 2 is attached. In the elastic tubes 1 shown in FIG. 3, illustration of the fixing portion is omitted for the convenience of description.

In FIG. 4(a), the non-stretching body 4 acts to prevent (suppress) the inflation of the elastic tube 1. Specifically, the elastic tube 1 does not inflate on the fixing portion side even when the portion of the elastic tube 1 that is on the opposite side of the fixing portion, in which the non-stretching body 4 is embedded and fixed (the middle upper side of the elastic tube 1k in FIG. 3(a)), inflates upon increase in the pressure of air W contained in the elastic tube 1. This enables the articulated bending portion 30 to curve downward in the drawing (to the opposite side of the inflated portion P) as illustrated in FIG. 3(b). Thus, by changing the pressure of air W in the elastic tube 1a, the curving angle of the articulated bending portion 30 can be changed as desired.

Figure 18:
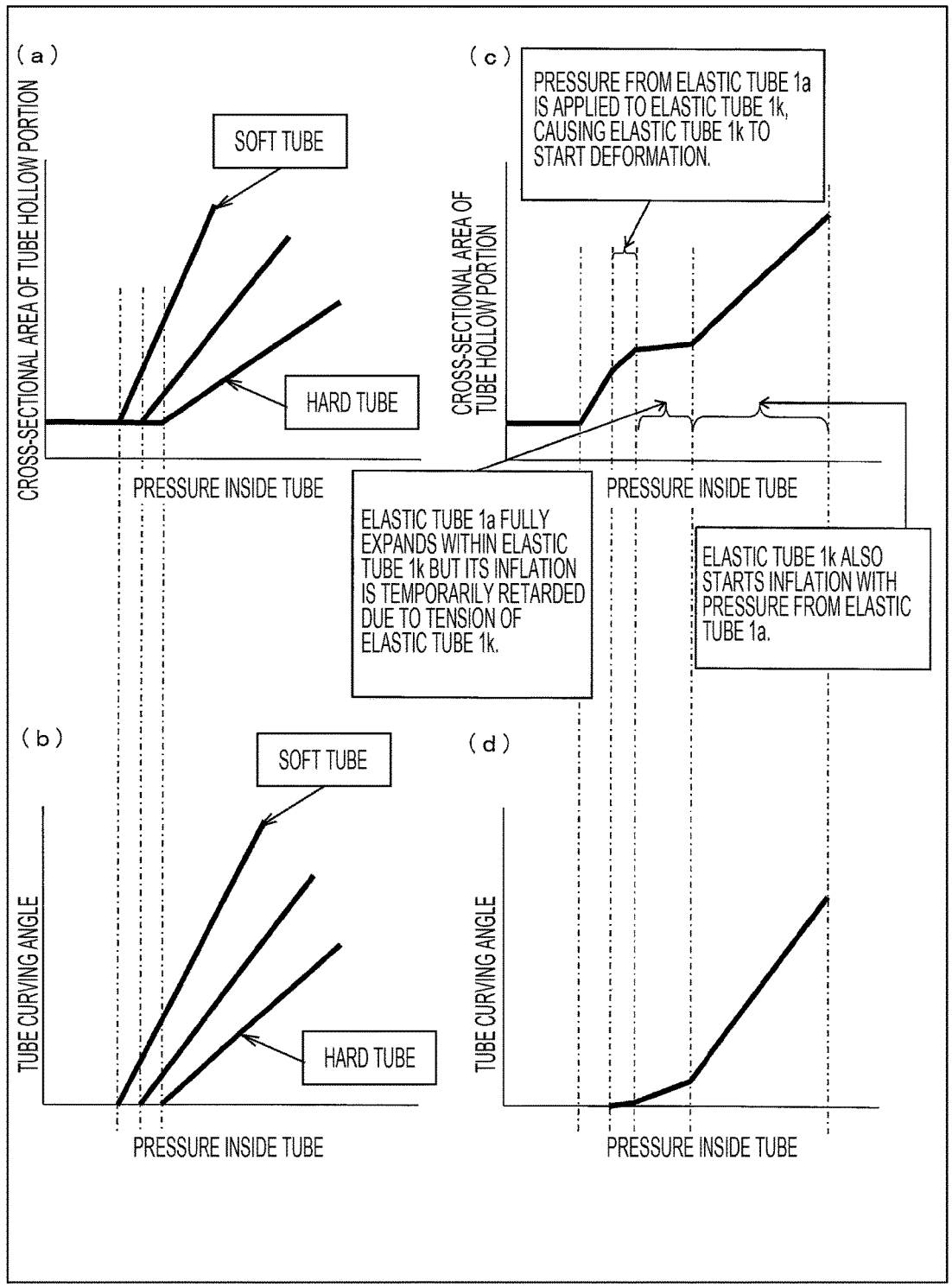
FIG. 18 shows graphs showing the relation between the internal pressure of an elastic tube according to Embodiment 1 of the present invention and the cross-sectional area of the hollow portion and the curving angle of the elastic tube.
Figure 19:
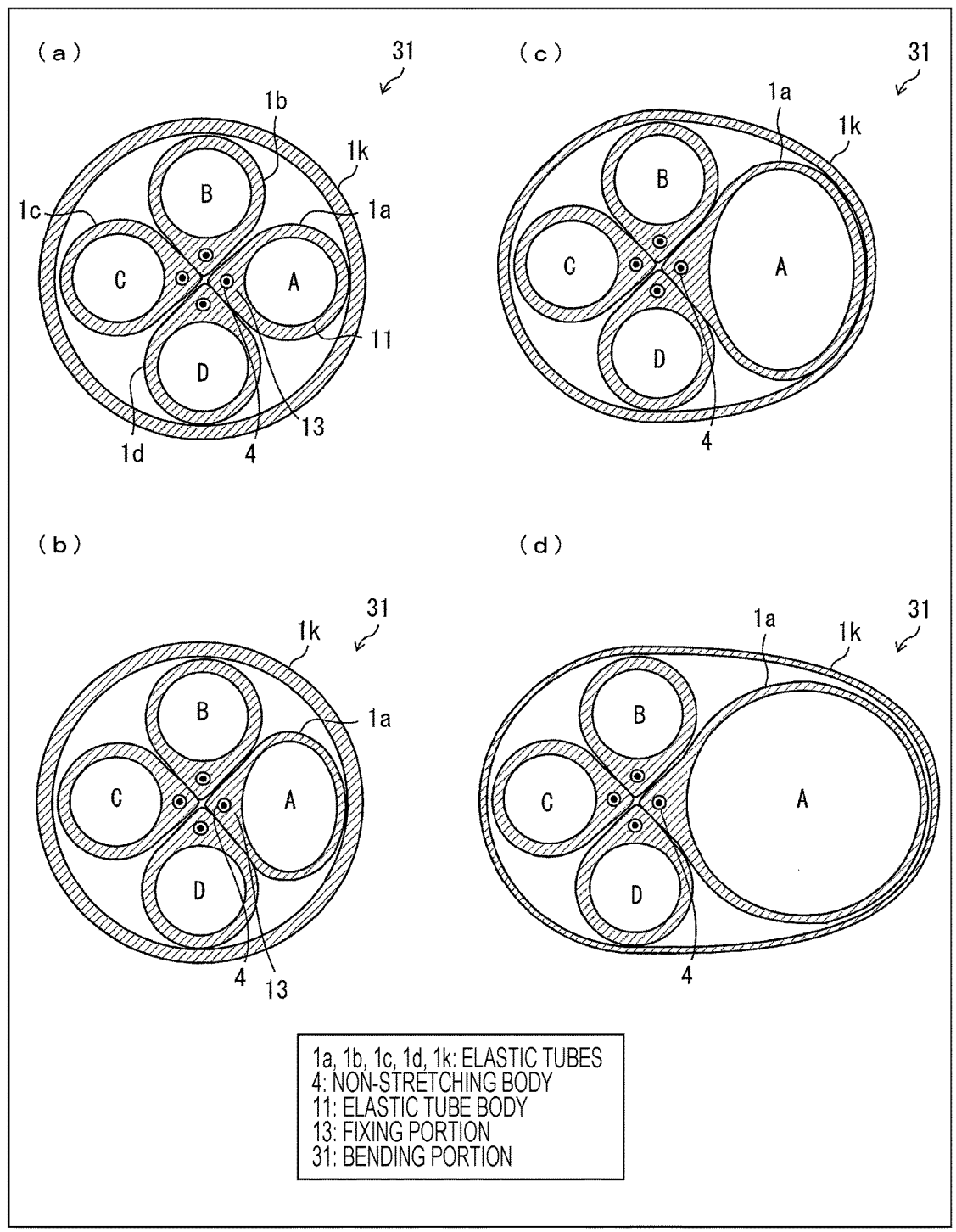
FIG. 19 shows cross-sectional views of the articulated bending portion according to Embodiment 1 of the present invention, sequentially illustrating states of tube A as it is pressurized.

Using FIGS. 18 and 19, the behaviors of an elastic tube and an elastic tube positioned around it when the inside of the former elastic tube is pressurized will be described in detail.

First, a graph showing the relation between the internal pressure and the cross-sectional area of the hollow portion of a single elastic tube alone as a basic component when it is pressurized is provided in FIG. 18(a), and a graph showing the relation between the internal pressure and the curving angle is provided in FIG. 18(b). As shown in FIG. 18(a), as the elastic tube is pressurized, in the beginning, it does not inflate in response to the pressurization because of its tension, but starts to inflate at the point its internal pressure has exceeded the tension, causing the cross-sectional area to increase and also the elastic tube to start bending. The bending motion depends on the wall thickness of the elastic tube and the elastic modulus of its material. For instance, as shown in FIGS. 18(a) and 18(b), a soft tube starts bending at a low pressure and bends largely, whereas a hard tube starts bending at a relatively high pressure and makes a relatively small bend. Thus, bending motion characteristics can be set as desired based on the design of the structure or material of the elastic tube.

Next, using FIGS. 18 and 19, a case of pressuring the inside of tube A in a bending portion 31 having the structure of FIG. 4 will be described as an illustrative example. FIG. 18(c) is a graph showing the relation between the internal pressure of tube A and the cross-sectional area of the hollow portion of tube A, and FIG. 18(d) is a graph showing the relation between the internal pressure of tube A and the curving angle of the elastic tube 1k.

As shown in FIGS. 18(c) and 19(a), as tube A is pressurized, in the beginning, the elastic tube 1a portion does not inflate inside the elastic tube 1k, but at the point the tension of the tube itself has been exceeded, only the elastic tube 1a portion starts to inflate.

Then, as tube A is gradually pressurized as shown in FIG. 19(b), inflation of tube A is temporarily retarded at the point when the pressure from the elastic tube 1a is applied to the elastic tube 1k.

As pressurization is further continued, the tube A and the elastic tube 1k start inflating at the same time as shown in FIG. 19(c), causing a substantial bend to start as shown in FIG. 19(d).

Accordingly, the relation between the internal pressure of tube A and the cross-sectional area of its hollow portion exhibits a step-wise increase of the cross-sectional area. The relation between the internal pressure of tube A and the curving angle exhibits a step-wise bending motion as shown in FIG. 18(d). That is, the bending angle of the elastic tube 1k changes stepwise in response to increase of the pressure inside tube A. The bending motion is also dependent on the size, wall thickness and material elastic modulus of the elastic tube 1k in addition to those of the elastic tube 1a, so bending motion characteristics can be set as desired based on these structural or material designs.

Such a stepwise bending motion of the elastic tube 1k described above occurs not only during an increase of the internal pressure of tube A but during a decrease (drop) of the pressure.

Additionally, the presence of the elastic tube 1k on the periphery can yield a distinctive effect of suppressing inflation in the elastic tube circumferential direction (the lateral direction), which do not contribute to bending, and effectively creating a bend caused by inflation in the long-axis direction (the vertical direction), which directly affects the control of the curving angle. Further, since unnecessary inflation in the elastic tube circumferential direction is suppressed, degradation of elastic tubes caused by mechanical stress that occurs from repeated inflations and deflations can be prevented as well.

It is desirable that the air pressure W when the elastic tube is not bent be set to the pressure immediately before the elastic tube starts bending. This can prevent bending of the elastic tube caused by its own weight and keep the elastic tube in a straight linear shape.

The non-stretching body 4 has any stretchability lower than that of the elastic tube body 11 that is sufficient to allow the portion of the elastic tube body 11 opposite the fixing portion 13 (the thick wall portion on the opposite side of where the non-stretching body 4 is disposed) to inflate in the circumferential direction and prevent inflation of the elastic tube body 11 on the fixing portion 13 side. The material of the non-stretching body 4 may be non-stretching thread (fishing line) made of glass fiber or polyamide fiber, for example, or silicone, that is, the same material as the elastic tube 1.

The non-stretching body 4 may also be a cable connected with the medical device. For example, an electric cord for supplying power to the endoscope camera 2 may double as the non-stretching body 4 shown in FIG. 4(a). Alternatively, a cable that connects between the endoscope camera 2 and a camera monitor (not shown) along the endoscope part 10 shown in FIG. 1 may double as the non-stretching body 4. The non-stretching body 4 and a cable connected with the medical device may be fixed inside the elastic tube body 11.

(Connection from the Articulated Bending Portion to the Control Device)

The non-inflating tube is formed of a linear, hard hollow member having a length of about 2 cm to 30 cm (which is not limitative and the length is desirably set to an appropriate size depending on the number of joints) that has the same shape as the articulated bending portion 30, namely the same outer and inner diameters as the elastic tube body 11. The non-inflating tube may be fabricated from acrylic resin.

In FIG. 1, the connecting tube 5 is a tube connecting between the endoscope part 10 and the control device 20. The connecting tube 5 is a hollow, cylindrical tube which is flexible and non-inflatable, and is connected with the non-inflating tube. The connecting tube 5 has a shape substantially the same as the non-inflating tube and is about 2 m long, communicating with the elastic tube 1 and the non-inflating tube. The connecting tube 5 contains air W. The non-bending portion 32 at the proximal end side may be held on a flexible stand. This would permit the direction of the articulated bending portion 30 to be changed as desired using the flexible stand.

The connecting tube 5 may consist of multiple connecting tubes, depending on the configuration of the pressurization mechanism for the elastic tubes.

(Hollow Interior of the Elastic Tube)

FIG. 3(c) is a cross-sectional view of the elastic tube 1a as an example and the non-inflating tube 3a in the long-axis direction as seen from the arrow in line C-C' in FIG. 3(a). As shown in FIGS. 3(c) and 5, the non-inflating tube 3a is structured by wrapping the non-inflating body 34 around the elastic tube 1a.

FIG. 3(d) shows another example of the structure of the elastic tube 1a and the non-inflating tube 3a. As shown in FIG. 3(d), the elastic tube 1a and the non-inflating tube 3a may be separate components which are coupled together by bonding such that their hollow portions communicate with each other. (As the hollow portion of the elastic tube 1a communicates with that of the non-inflating tube 3a, they are collectively termed as tube A. The same applies to tube B and so on.) The hollow portion of the elastic tube 1a and so on contains air W supplied by the control device 20 from the side of the connecting tube 5 through the non-inflating tube.

The non-stretching body 4 is very thin relative to the elastic tube body 11; for example, when the outer diameter of the elastic tube body 11 in cross section is 2 mm, the outer diameter of the non-stretching body 4 in cross section is about 0.3 to 0.5 mm. The cross section of the non-stretching body 4 is not limited to a circular shape but may be a polygonal shape, such as a triangle or square, that is chamfered so as not to damage the human body when inserted into the body and small in size.

Although not shown, the elastic tube 1 may also be structured such that the fixing portion 13 (not shown) is positioned on the outer circumferential surface (the exterior) of the elastic tube body 11. In that case, the non-stretching body 4 is fixed to the exterior of the elastic tube body 11.

If a cable connected with a medical device (for example, an electric cord) doubles as the non-stretching body 4, the non-stretching body 4 (or the electric cord) is bonded to the side surface of the non-inflating tube (see FIG. 1) in addition to the fixing portion 13 of the elastic tube 1, and drawn outside the endoscope part 10.

The elastic tube may also be structured such that the fixing portion is positioned on the inner circumferential surface (the interior) of the elastic tube body 11. In that case, the non-stretching body 4 is fixed to the interior of the elastic tube body 11. A cable connected with a medical device may also double as the non-stretching body 4.

With such a configuration, because the non-stretching body 4 and the cable connected with the medical device are fixed on the interior of the elastic tube body 11, no unevenness would occur on the surface of the elastic tube body 11 if the elastic tubes are exposed on the outermost surface. This makes the elastic tube 1k easy to wash and sterilize, facilitating its reuse.

In addition, with the aforementioned configuration, the non-stretching body 4 and the cable connected with the medical device are fixed on the interior of the elastic tube body 11, thus placed in locations protected by the elastic tube body 11. Accordingly, if part of the non-stretching body 4 and the cable connected with the medical device is broken for some reason, the broken part is protected by the elastic tube body 11, thus lowering the risk of damage to the human body. For example, if part of the non-stretching body 4 is broken for some reason, the risk of the broken part of the non-stretching body 4 damaging the human body is low even when the non-stretching body 4 has lower stretchability than the elastic tube. As another example, if the cable connected with the medical device is an electric cable, adverse effects such as current leakage due to breakage of the electric cable can be avoided in the human body. Besides, since gas is injected in the elastic tube body 11, should the electric cable is broken, adverse effects of current leakage can be avoided in the elastic tube body 11 because electrical conductivity in the elastic tube body 11 is low.

In a case where a non-stretching body 4 different from the cable connected with the medical device is fixed to the elastic tube body 11, the cable connected with the medical device may be disposed in the hollow interior of the elastic tube body 11. For instance, in a case where the fixing portion is disposed on the inner circumferential surface (the interior) of the elastic tube body 11, a non-stretching body 4 different from the cable connected with the medical device may be fixed on the interior of the elastic tube body 11 and the cable 14 connected to the medical device may be disposed in the hollow interior of the elastic tube body 11.

The elastic tube may also be structured such that the fixing portion is disposed inside the elastic body of the elastic tube body 11. The elastic body is the constituent of the elastic tube body 11, forming the thickness portion from the inner circumferential surface to the outer circumferential surface of the elastic tube body 11. More specifically, the elastic tube is structured such that the fixing portion is disposed between the inner circumferential surface and the outer circumferential surface of the elastic tube body 11. Accordingly, the non-stretching body 4 is fixed so as to be embedded between the inner circumferential surface and the outer circumferential surface of the elastic tube body 11. That is, an elastic tube body 11 having such a structure permits the non-stretching body 4 to be fixed to the elastic tube body 11 by advance formation of the non-stretching body 4 as an integral part of the elastic tube body 11. A cable 14 connected with a medical device may double as the non-stretching body 4 as well.

In a case where the non-stretching body 4 is provided separately from a cable connected with a medical device, the non-stretching body 4 may be fixed so as to be embedded between the inner circumferential surface and the outer circumferential surface of the elastic tube body 11, and the cable 14 may be disposed in the hollow interior of the elastic tube body 11. In addition, although the non-stretching body 4 or the cable 14 may be configured to be in contact with the outer circumferential surface and inner circumferential surface of the elastic tube body 11, it is desirable that they be disposed spaced apart from the outer circumferential surface or inner circumferential surface of the elastic tube body 11 in order to enhance the mechanical strength of the elastic tube.

With the foregoing configuration, the non-stretching body 4 and the cable connected with the medical device are embedded between the inner circumferential surface and the outer circumferential surface of the elastic tube body 11, so no unevenness would occur on the surface (the outer circumferential surface) of the elastic tube body 11. This makes the elastic tubes easy to wash and sterilize to facilitate their reuse even when the elastic tubes are exposed on the outermost surface.

With the above-described configuration, the non-stretching body 4 and the cable connected with the medical device are in locations protected by the elastic tube body 11 because they are fixed between the inner circumferential surface and the outer circumferential surface of the elastic tube body 11 or to the hollow interior of the elastic tube body 11. Thus, if part of the non-stretching body 4 and the cable connected with the medical device is broken for some reason, the broken part is protected by the elastic tube body 11, thus lowering the risk of damage to the human body.

For example, if part of the non-stretching body 4 is broken for some reason, the risk of the broken part of the non-stretching body 4 damaging the human body is low even when the non-stretching body 4 has lower stretchability than the elastic tube. As another example, if the cable connected with the medical device is an electric cable, adverse effects such as current leakage caused by breakage of the electric cable can be avoided in the human body. Besides, since gas is injected in the elastic tube body 11, should the electric cable is broken, adverse effects of current leakage can be avoided in the elastic tube body 11 because electrical conductivity in the elastic tube body 11 is low.

In addition, with the foregoing configuration, the outer circumferential surface of the non-stretching body 4 or the cable connected with the medical device is entirely fixed to the elastic tube body 11. Thus, the curving angle θ of the elastic tube changes at a constant rate in relation to the level of the pressure P of the air present in the hollow interior of the elastic tube body 11. This provides the advantage of facilitating the control of the curving angle θ of the elastic tube body 11.

With the foregoing configuration, the aforementioned adverse effects on the human body that could be caused by the cable 14 connected to the medical device can be avoided. Further, because the portion around the medical device mounted to the elastic tube 1 can be made compact, a cable connected with the medical device will not interfere with a medical procedure.

(Overview of the Control Device)

The control device 20 in FIG. 1 will be described. Note that the following description presents an example of the control device 20 and is not intended to limit the configuration of the control device. The control device 20 can have any of various configurations that are capable of pressurizing the tubes contained in the articulated bending portion 30, without being limited to the configuration described below.

The control device 20 includes a piston (air pressure varying unit, a fluid pressure varying unit) 21 and a syringe 22 for changing the pressure of air (gas) W in the elastic tube 1, an air pressure sensor 23 for detecting the pressure of air W, a piston driving unit (an air pressure varying unit) 24 for actuating the piston 21 in the syringe 22 and varying the air pressure in the elastic tube 1, a microphone (instruction receiving unit) 25 to which voice of the operator (instructions) is input, and a pressurization control unit (an air pressure varying unit) 26 for controlling the piston driving unit 24. The pressurization control unit (air pressure varying unit) 26 may be configured to receive voice signals input through the microphone 25, and detection signals from the air pressure sensor 23 as input and control the piston driving unit 24, for example. The gas contained in the elastic tube 1 is not limited to air, but can be any kind of gas that does not contaminate the treated site.

The control device 20 also includes a pressurizing valve driving unit 28. The pressurizing valve driving unit 28 rotates the pressurizing valve 36 in response to control by the pressurization control unit 26.

While this embodiment uses the piston 21, piston driving unit 24, and pressurization control unit 26 as examples of air pressure varying units, they may be replaced with an air pressure regulating valve or the like. Also, a foot switch or the like may be used instead of the microphone.

(Manipulation Through the Control Device)

A scenario in a medical procedure (an operation) will be described below. In response to the voice of the operator detected by the microphone, the pressurization control unit 26 controls the piston driving unit 24 so as to change the air pressure in the elastic tube 1 using the piston 21 and the syringe 22.

For instance, in a situation where the endoscope camera 2 is able to curve upward or downward on the display screen of a camera monitor, if the operator says "up", the image being displayed on the display screen of the camera monitor starts to move so as to show the upper side of the image. Then, in response to the operator saying "stop", the image on the display screen of the camera monitor stops moving. If the operator says "down", the image being displayed on the display screen of the camera monitor moves downward.

After being used in a medical procedure or the like, the elastic tube 1 can be replaced with a new elastic tube 1 (that is, is disposable). Alternatively, a used elastic tube 1 can be used again (reused) after completion of a medical procedure by washing and disinfecting it. When elastic tubes 1 are reused, for preventing use of degraded elastic tubes 1, it is required to preset an upper limit number of times the elastic tube 1 can be used or curved in the control device 20 and prohibit use of an elastic tube 1 that has been used or curved the upper limit number of times.

(Specific Example of the Control Device)

The piston 21 is slidably inserted in the syringe 22 connected with connecting tube 5. The piston 21 may also be configured to be fit on a screw portion coupled to the piston driving unit 24 so that the piston driving unit 24 makes the piston 21 slide within the syringe 22 by rotating the screw portion positively or negatively. Whether the piston driving unit 24 rotates positively or negatively and the number of rotations are controlled by the pressurization control unit 26.

(Curving Angle of the Elastic Tube)

The curving characteristics of the elastic tube in an embodiment of the present invention will be described below based on the relation between the air W present in the elastic tube body 11 and the curving angle of the elastic tube body 11.

First, they will be described by taking as an example a configuration in which the non-stretching body 4 is fixed to the outer circumferential surface or the inner circumferential surface of the elastic tube body 11.

For example, when the pressure P of air W in the elastic tube body 11 is increased (during pressurization), the curving angle θ of the elastic tube 1 gently increases monotonously in response to increase of the air pressure until the pressure is around 230 kPa. After the pressure P has increased past around 230 kPa, the curving angle θ of the elastic tube 1 sharply increases relative to increase in pressure P. When the pressure P of air W in the elastic tube body 11 is decreased (during depressurization), the curving angle θ of the elastic tube 1 gently decreases monotonously in response to decease in pressure P until the pressure P is around 230 kPa. After pressure P decreased below around 230 kPa, the curving angle θ of the elastic tube body 11 sharply decreases relative to decrease of pressure P until the pressure P is around 170 kPa. Then, after pressure P has decreased below around 170 kPa, the curving angle θ of the elastic tube body 11 again gently decreases monotonously in response to decrease in pressure P.

By presetting such curving characteristics of the elastic tube body 11 in the pressurization control unit 26, the curving angle of the elastic tube body 11 can be changed so that the image being displayed on the camera monitor moves at a constant rate.

Next, the curving characteristics will be described by taking a case where the non-stretching body 4 is fixed so as to be embedded between the inner circumferential surface and the outer circumferential surface of the elastic tube body 11 as an example.

For example, when the pressure P of air W in the elastic tube body 11 is increased (during pressurization), the curving angle θ of the elastic tube 1b increases almost linearly in response to increase in the air pressure from a pressure of around 100 kPa to around 260 kPa. When the pressure P of air W in the elastic tube body 11 is decreased (during depressurization), the curving angle θ of the elastic tube 1b linearly decreases in response to decrease in pressure P from a pressure P of around 260 kPa to around 100 kPa.

As shown above, during both pressurization and depressurization, the curving angle θ of the elastic tube 1*b* changes at a corresponding constant rate each time there is an increase or decrease in pressure P, without causing large hysteresis characteristics. Also, the relation between pressure P and angle θ during pressurization is substantially equal to the relation between pressure P and angle θ during depressurization.

By presetting such curving characteristics of the elastic tube body 11 in the pressurization control unit 26, the curving angle of the elastic tube body 11 can be changed so that the image being displayed on the camera monitor moves at a constant rate. Moreover, since the curving characteristics of the elastic tube body 11 are linear in the above example, setting of the pressurization control unit 26 will be simpler when an elastic tube body 11 with linear characteristics is used than when an elastic tube 1 with hysteresis characteristics is used. This provides the advantage of facilitating the control of the curving angle of the elastic tube body 11.

(Exemplary Manipulation of the Elastic Tube)

The elastic tube 1 may also be adapted for automated manipulation. For example, if the endoscope camera 2 shown in FIG. 1 is used as a medical device, an arrangement (not shown) may be employed in which an image captured by the endoscope camera 2 is displayed on the camera monitor and at the same time the image captured by the endoscope camera 2 is acquired and analyzed by the control device 20. The control device 20 automatically adjusts the pressure of the gas contained in the elastic tube body 11 based on information analyzed. The curving angle of the endoscope camera 2 thus can be changed in an automated manner. The control device 20 has prestored therein image data indicative of the progress of a medical procedure or the like. The control device 20 may also change the curving angle of the endoscope camera 2 using the hysteresis characteristics described above.

The elastic tube 1 may also be manually operated using a tablet terminal. For example, when an assistant of the operator conducting a medical procedure manipulates a tablet terminal to change the curving angle of a medical instrument, the assistant can manipulate the tablet terminal at a location away from the operator. Thus, manipulation by the assistant does not interfere with the medical procedure actions being performed by the operator, allowing the operator to concentrate on the medical procedure. Alternatively, the operator may manipulate a tablet terminal to change the curving angle of the medical instrument, for example. In such a case, a robot can be made perform the actual medical procedure on behalf of the operator.

[Embodiment 2]

Another embodiment of the present invention will be described below based on FIGS. 7 to 9. For the sake of description, components having the same functionality as ones described in the previous embodiment are denoted with the same reference numerals and description of such components is omitted.

Embodiment 1 mainly described a movable mechanism with a single bending portion in detail, while Embodiment 2 will describe a movable mechanism that operates by coordinating two bending portions in combination.

(Overview of the Articulated Bending Portion)

Figure 7:
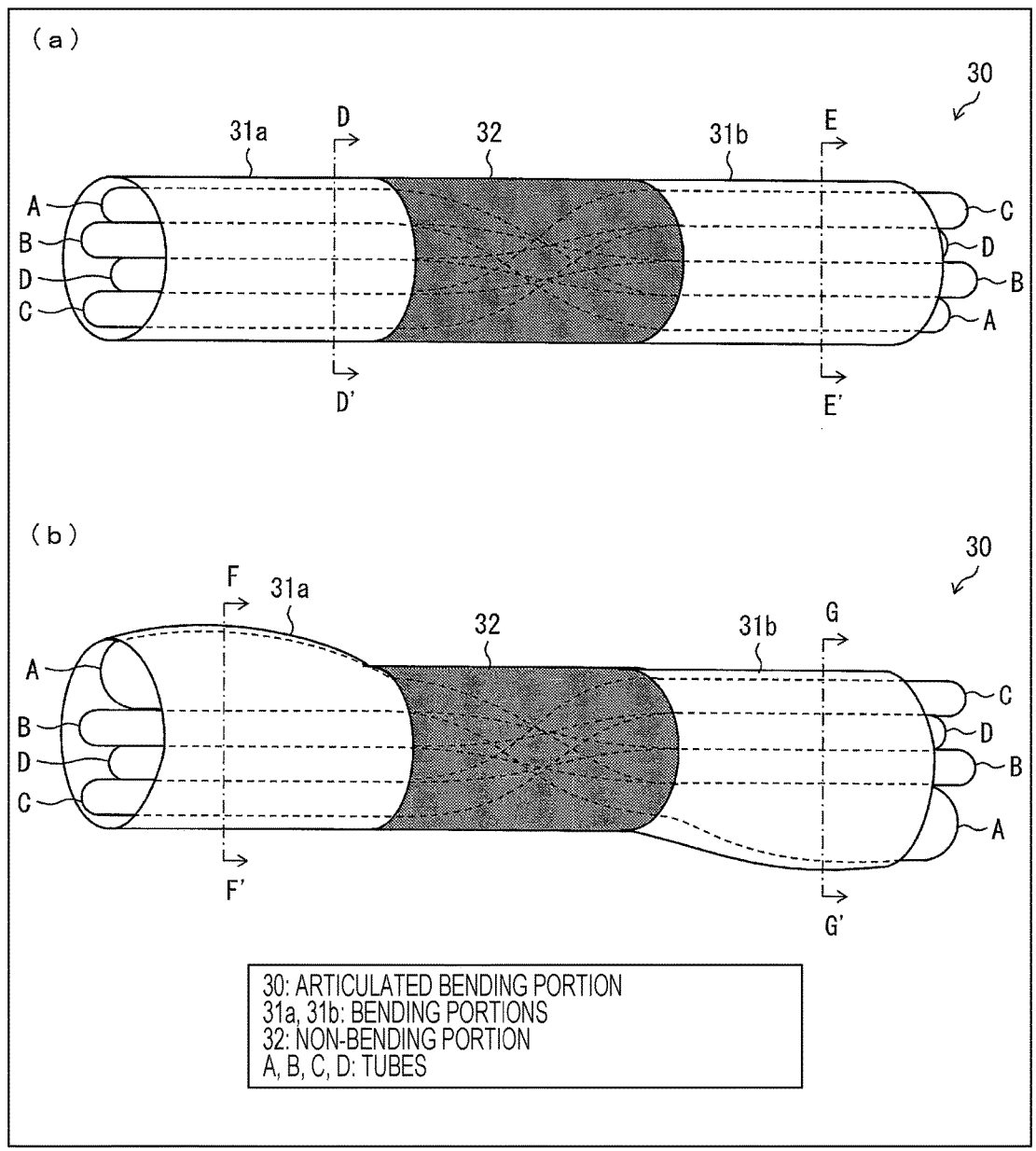
FIG. 7 shows perspective views showing an example of the internal structure of bending portions and a non-bending portion of the articulated bending portion according to Embodiment 2 of the present invention, where

FIG. 7 shows an example of a movable mechanism that operates by coordinating two bending portions in combination. While the configuration with four elastic tubes 1*a* to 1*d* forming the articulated bending portion is similar to Embodiment 1, the position of each of the elastic tubes 1*a* to 1*d* is interchanged with the opposite tube in the non-bending portion 32 as illustrated in FIG. 7.

Figure 8:
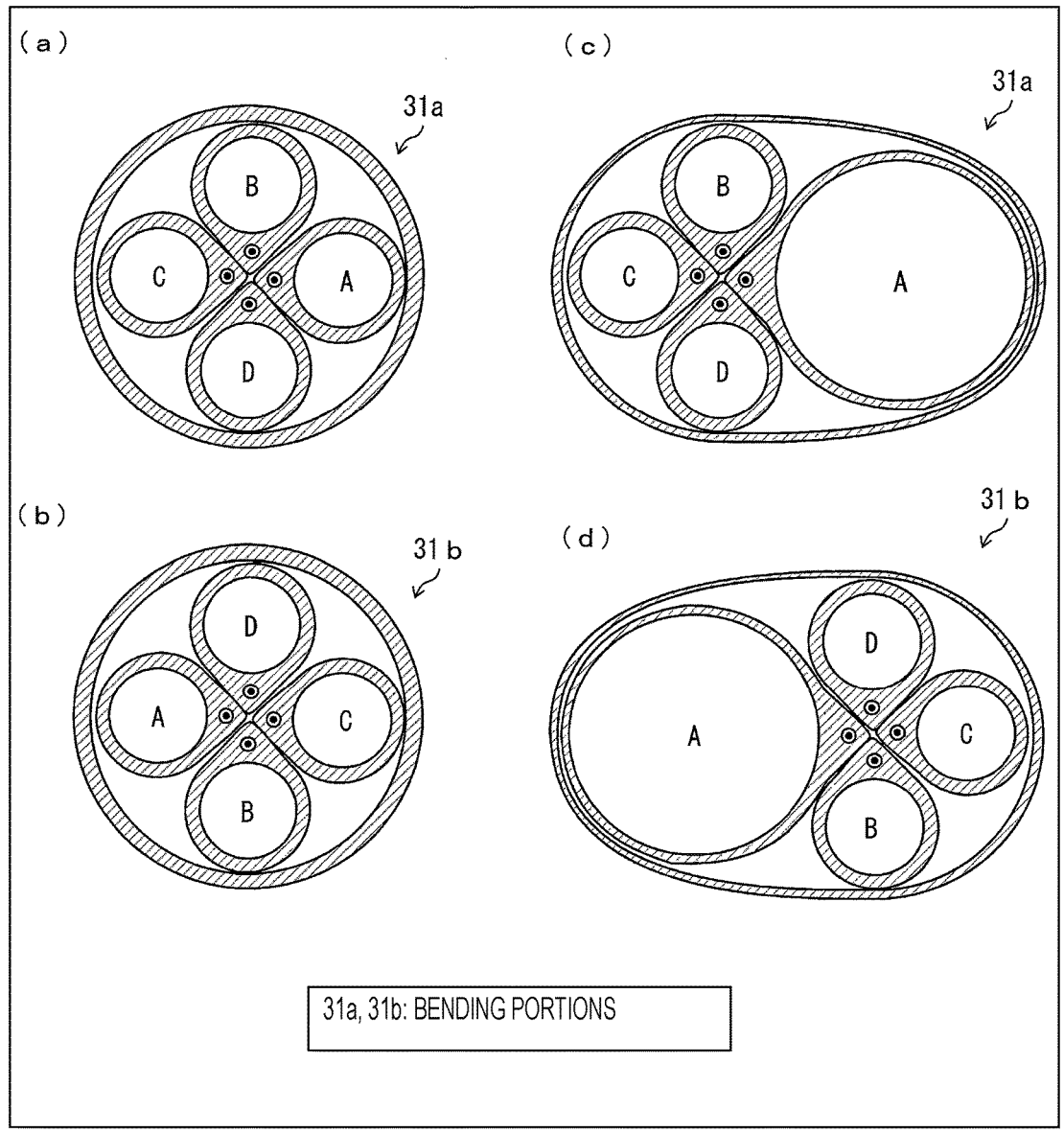
FIGS. 8(a) to 8(d) are cross-sectional views of the articulated bending portion in Embodiment 2.

FIG. 8(*a*) is a cross-sectional view seen from the arrow in line D-D' in FIG. 7(*a*); FIG. 8(*b*) is a cross-sectional view seen from the arrow in line E-E' in FIG. 7(*a*); FIG. 8(*c*) is a cross-sectional view seen from the arrow in line F-F' in FIG. 7(*b*); and FIG. 8(*d*) is a cross-sectional view seen from the arrow in line G-G' in FIG. 7(*b*).

As an example, as shown in the cross-sectional views of FIGS. 8(*a*) and 8(*b*), the elastic tube 1*a* can be interchanged with 1*c* and also 1*b* can be interchanged with 1*d*. This can be considered as a characteristic feature enabled by independent elastic tubes.

As shown in FIGS. 7(*b*), 8(*c*), and 8(*d*), for example, when the elastic tube 1*a* is pressurized with the pressure of air W injected from the control device 20, inflation in opposite directions occurs in the bending portions (joints) 31*a* and 31*b*. Thus, bends in opposite directions can be produced in two bending portions as illustrated in FIGS. 9(*a*) and 9(*b*).

By making settings so that the bending angles of the two bending portions are the same, the distal end portion can be steered without changing the orientation of the distal end portion unlike Embodiment 1. This provides a distinctive effect of yielding an image very easy for the operator to see especially when the distal end portion is equipped with a camera because the field of view can be moved without changing the angle of view.

Also, similarly to Embodiment 1, as the bending motions in the two bending portions 31*a* and 31*b* are dependent on the size and wall thickness, the elastic modulus of the material, the self-weight to be born of not only the elastic tube 1*a* but the elastic tube 1*k*, the bending portions can be designed to have the same bending motion characteristics based on such structural and/or material designs.

Additionally, the presence of the elastic tube 1*k* on the outer periphery can create a distinctive effect of suppressing the inflation in the elastic tube circumferential direction (the lateral direction), which do not contribute to bending, and effectively creating a bend caused by inflation in the long-axis direction (the vertical direction), which directly affects the control of the curving angle. Further, since unnecessary inflation in the elastic tube circumferential direction is suppressed, degradation of elastic tubes caused by mechanical stress that occurs from repeated inflations and deflations can be prevented as well.

As in Embodiment 1, bends in four directions can be produced by pressurizing the individual elastic tubes, and further a bend in an intermediate direction is also possible by selecting arbitrary two elastic tubes. That is, a rotational motion of the distal end portion such as shown in FIG. 9(*b*) or movement of the field of view in a desired direction can also be achieved by sequentially pressurizing the elastic tubes while adjusting the pressure.

Figure 9:
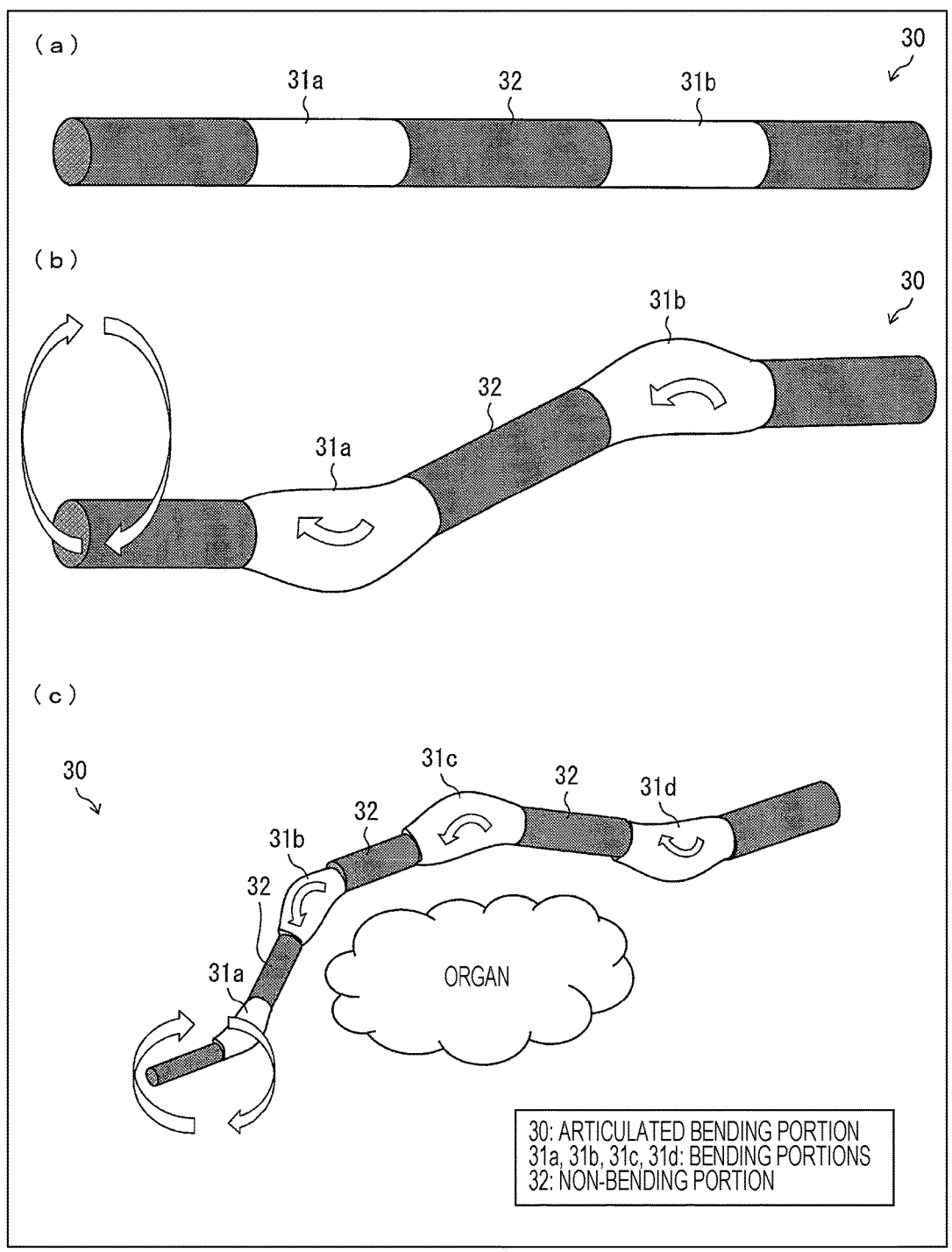
FIGS. 9(a) to 9(c) are perspective view illustrating the bending motion of the articulated bending portion in Embodiment 2.

As shown in FIG. 9(*c*), a set of bending portions 31 bend in a particular direction depending on the positions of the tubes incorporated therein in advance. For example, bends in opposite directions can be produced by interchanging the positions of the elastic tubes 1*a* to 1*d* with the opposite tubes in a non-bending portion 32 as described above, or bends shifted by 90 degrees can be produced by interchanging each tube with a neighboring tube.

For such multiple bending points, the pressure at which they start bending may be adjusted by appropriately combining the aforementioned various features so that bending motions simultaneously occur in all of the bending points or bends occur sequentially starting from the bending point at the distal end, for example.

In this way, a variety of bending directions and bending motions are possible based on the combination of the positions and bending characteristics of the tubes incorporated in advance and the amount of pressurization for the four tubes. Specifically, by combining them with insertion or removal of pipes themselves and/or rotational motions, a wide variety of bending motions such as avoiding an organ or going behind an organ and viewing it from the back side (upward avoidance, rightward avoidance, leftward avoidance, or change of avoidance joint position) can be achieved. Specific examples of various bending motions will be shown in Embodiments 6 and 7 in detail.

[Embodiment 3]

Still another embodiment of the present invention will be described below based on FIG. 10. For the sake of description, components having the same functionality as ones described in the previous embodiments are denoted with the same reference numerals and description of such components is omitted.

Embodiments 1 and 2 mainly detailed a movable mechanism that has one or two bending portions, particularly in connection with application to a distal end portion having a camera attached thereon, while Embodiment 3 will describe a movable mechanism that operates with further increased bending portions in combination.

(Overview of the Articulated Bending Portion)

Figure 10:
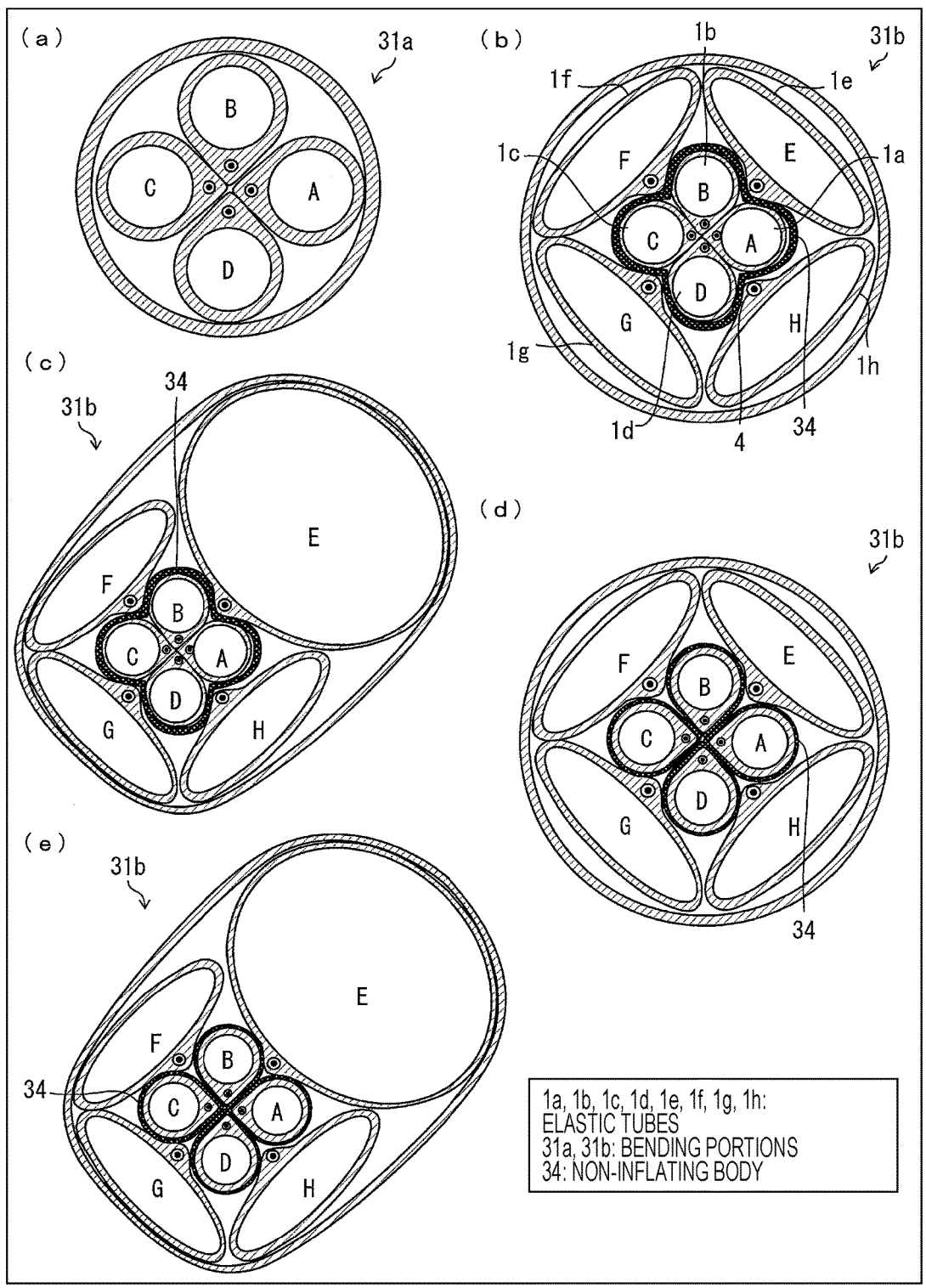
FIG. 10 shows cross-sectional views of the articulated bending portion according to Embodiment 3 of the present invention, where

FIG. 10 shows an example of a configuration with bending portions using the movable mechanism that operates with one or two bending portions in combination described in Embodiments 1 and 2 for the distal end portion having a camera attached thereon and using the configuration described in Embodiment 2 in the middle and proximal end portions.

The configuration of a bending portion 31a on the distal end portion side is shown in FIG. 10(a), though detailed description is omitted as it has been already described in Embodiments 1 and 2.

The cross-sectional structure of the bending portion 31b on the middle and proximal end side is shown in FIG. 10(b). The elastic tubes 1a to 1d for use in the distal end portion are structured such that the non-inflating body 34 is wrapped around them inside the bending portion 31b. This allows the bending portion 31a to bend without causing the bending portion 31b to bend by pressurizing the elastic tubes 1a to 1d.

FIGS. 10(d) and 10(e) are cross-sectional views showing another example of the configuration of the bending portion 31b on the middle and proximal end portion side. For enhancing the non-inflatability, preventing interference with other tubes, and increasing the bend controllability, it is desirable that the non-inflating body 34 be wrapped around each of the elastic tubes 1a to 1d as shown in FIGS. 10(d) and 10(e).

For control of bending in the middle and proximal end portions, elastic tubes 1e to 1h are further disposed around the elastic tubes 1a to 1d. As to bending of the elastic tubes 1e to 1h, the foregoing description applies: a bending motion is produced by pressurizing and inflating the elastic tube 1e, for example, as shown in FIG. 10(c). With the configuration described above, bending of the bending portion 31a and the bending portion 31b can be controlled independently from each other.

As described in Embodiment 2, bends in opposite directions can be produced by interchanging the positions of the elastic tubes 1a to 1d with the opposite tubes in a non-bending portion 32, or bends shifted by 90 degrees can be produced by interchanging each tube with a neighboring tube, for example. Thus, a wide variety of bending motions such as avoiding an organ or going behind an organ and viewing it from the back side can be produced based on the positions of the tubes incorporated in advance. Specific examples of various bending motions will be shown in Embodiment 6 in detail.

[Embodiment 4]

Yet another embodiment of the present invention will be described below based on FIG. 11. For the sake of description, components having the same functionality as ones described in the previous embodiments are denoted with the same reference numerals and description of such components is omitted.

Embodiment 3 described a configuration that uses four elastic tubes for controlling the middle and proximal end portions, while Embodiment 4 shows an example that uses a single simplest elastic tube.

(Overview of the Articulated Bending Portion)

Figure 11:
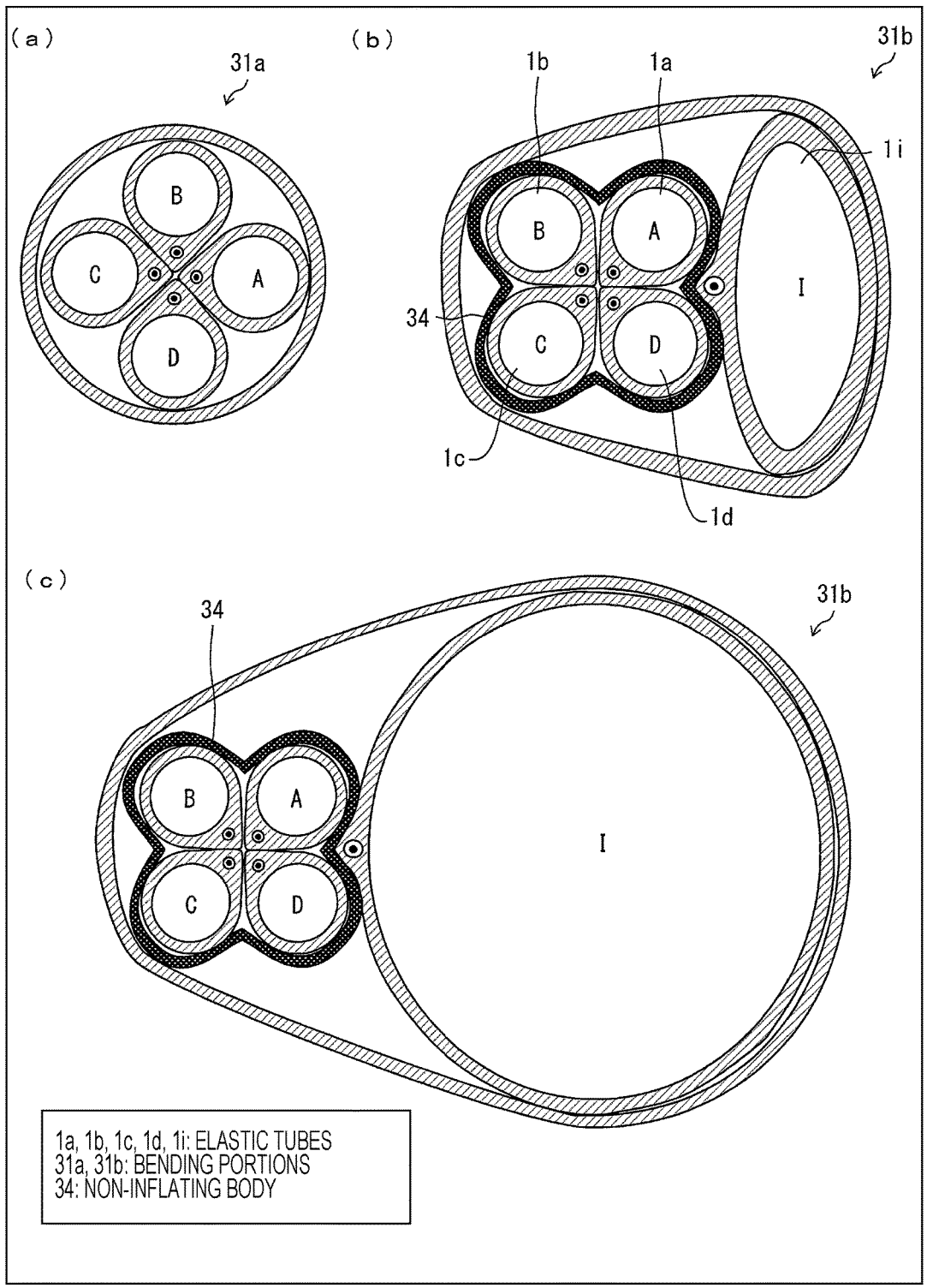
FIG. 11 shows cross-sectional views of the articulated bending portion according to Embodiment 4 of the present invention, where

FIG. 11 shows an example of a configuration with bending portions using the movable mechanism that operates with one or two bending portions in combination described in Embodiments 1 and 2 for the distal end portion having a camera attached thereon and using a single elastic tube for controlling the middle and proximal end portions.

The configuration of a bending portion 31a on the distal end portion side is shown in FIG. 11(a), though detailed description is omitted as it has been already described in Embodiments 1 and 2.

The cross-sectional structure of the bending portion 31b on the middle and proximal end side is shown in FIG. 11(b). The elastic tubes 1a to 1d for use in the distal end portion are structured such that the non-inflating body 34 is wrapped around them inside the bending portion 31b. This allows the bending portion 31a to bend without causing the bending portion 31b to bend by pressurizing the elastic tubes 1a to 1d.

Although not shown, for enhancing the non-inflatability, preventing interference with other tubes, and increasing the bend controllability, it is desirable that the non-inflating body 34 be wrapped around each of the elastic tubes 1a to 1d as in FIGS. 10(d) and 10(e).

For control of bending in the middle and proximal end portions, an elastic tube 1i is further disposed adjacent to the elastic tubes 1a to 1d. As to bending of the elastic tube 1i, the foregoing description applies: a bending motion is produced by pressurizing and inflating the elastic tube 1i as shown in FIG. 11(c). With the configuration described above, bending of the bending portion 31a and the bending portion 31b can be controlled independently from each other.

For example, bending in a particular direction can be achieved by fixing the position of the elastic tube 1i in a bending portion 31, or bending in a certain direction can be achieved by changing its position in another bending portion. In this manner, bending motions such as avoiding a predetermined organ or going behind an organ and viewing it from the back side can be produced based on the positions of the elastic tubes incorporated in advance. Because of a simple structure, there are not many other tubes that can be burden, enabling stable bending motions.

[Embodiment 5]

Yet another embodiment of the present invention will be described below based on FIGS. 12 and 13. For the sake of description, components having the same functionality as ones described in the previous embodiments are denoted with the same reference numerals and description of such components is omitted.

Embodiment 4 showed an example that uses a single simplest elastic tube for controlling the middle and proximal end portions, while Embodiment 5 shows another variation that uses a single simple elastic tube.

(Overview of the Articulated Bending Portion)

Figure 12:
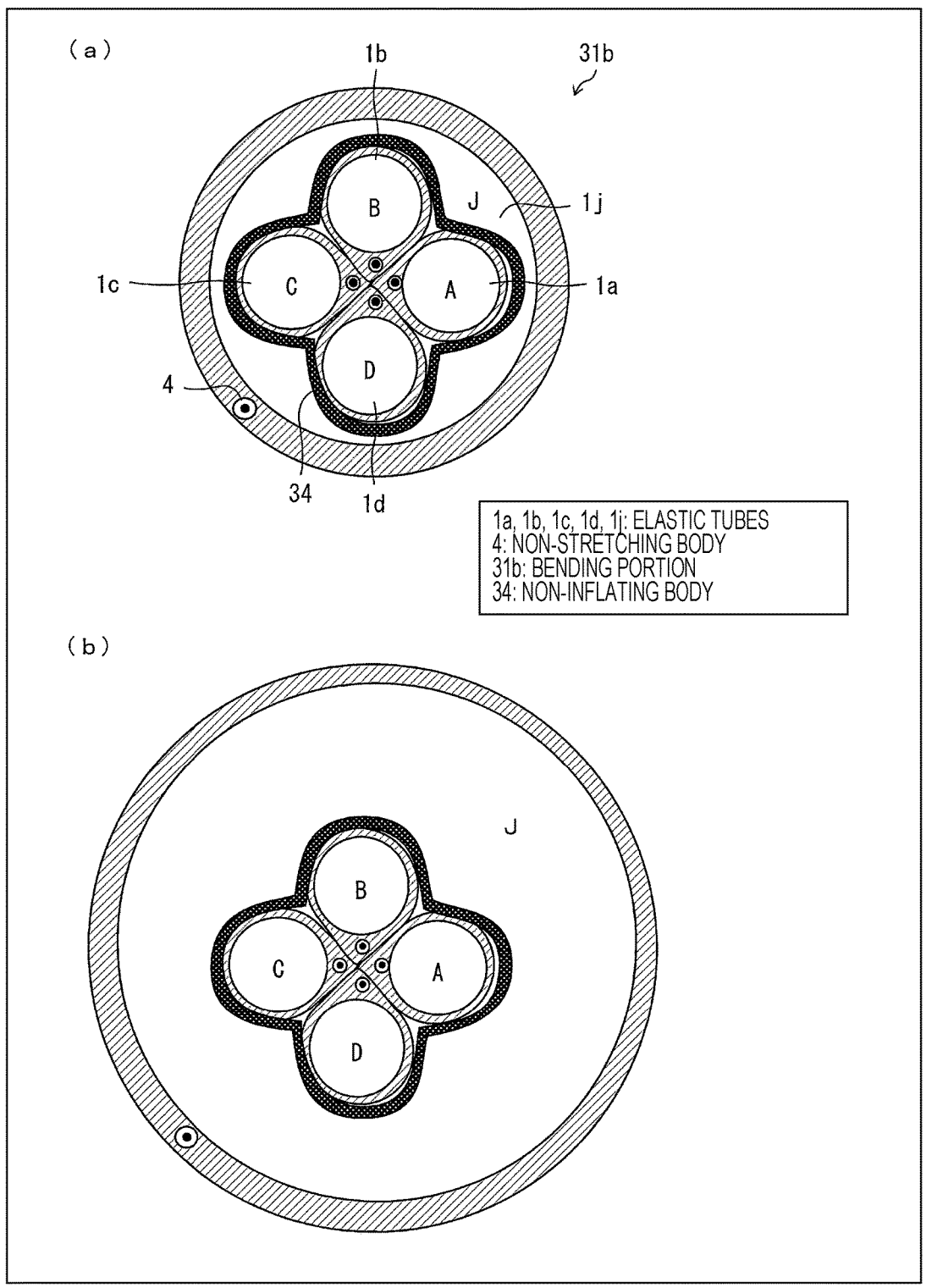
FIGS. 12(a) and 12(b) are cross-sectional views of the articulated bending portion according to Embodiment 5 of the present invention.

FIG. 12 shows another variation of the configuration with bending portions using the movable mechanism that operates with one or two bending portions in combination described in Embodiments 1 and 2 for the distal end portion having a camera attached thereon and using a single elastic tube for controlling the middle and proximal end portions.

Detailed description of the configuration of a bending portion 31a on the distal end portion side is omitted as it has been already described in Embodiments 1 and 2.

The cross-sectional structure of the bending portion 31b on the middle and proximal end side is shown in FIG. 12(a). An elastic tube 1j is used for controlling bending in the middle and proximal end portions, and the elastic tubes 1a to 1d for use in the distal end portion are disposed in the hollow interior of the elastic tube 1j. The elastic tube 1j has a structure in which the non-stretching body 4 is embedded between the inner circumferential surface and outer circumferential surface of the elastic tube 1j.

This configuration reduces burden on the bending motion of the elastic tube 1j caused by the elastic tubes 1a to 1d, so bending motion with better controllability can be achieved. The elastic tubes 1a to 1d for use in the distal end portion have a structure with the non-inflating body 34 wrapped around them. Although not shown, for enhancing the non-inflatability, preventing interference with other tubes, and increasing the bend controllability, it is desirable that the non-inflating body 34 be wrapped around each of the elastic tubes 1a to 1d as in FIGS. 10(d) and 10(e).

Further, as to bending of the elastic tube 1j, the foregoing description applies: a bending motion is produced by pressurizing and inflating the elastic tube 1j as shown in FIG. 12(b). For example, bending in a particular direction can be achieved by fixing the position of the non-stretching body 4 of the elastic tube 1j in a bending portion 31, or bending in a certain direction can be achieved by changing the position of the non-stretching body 4 in another bending portion. In this manner, bending motions such as avoiding a predetermined organ or going behind an organ and viewing it from the back side can be produced based on the position of the non-stretching body 4 embedded in the elastic tube in advance. Because of a simple structure, there are not many other tubes that can be burden, enabling stable bending motions.

Figure 13:
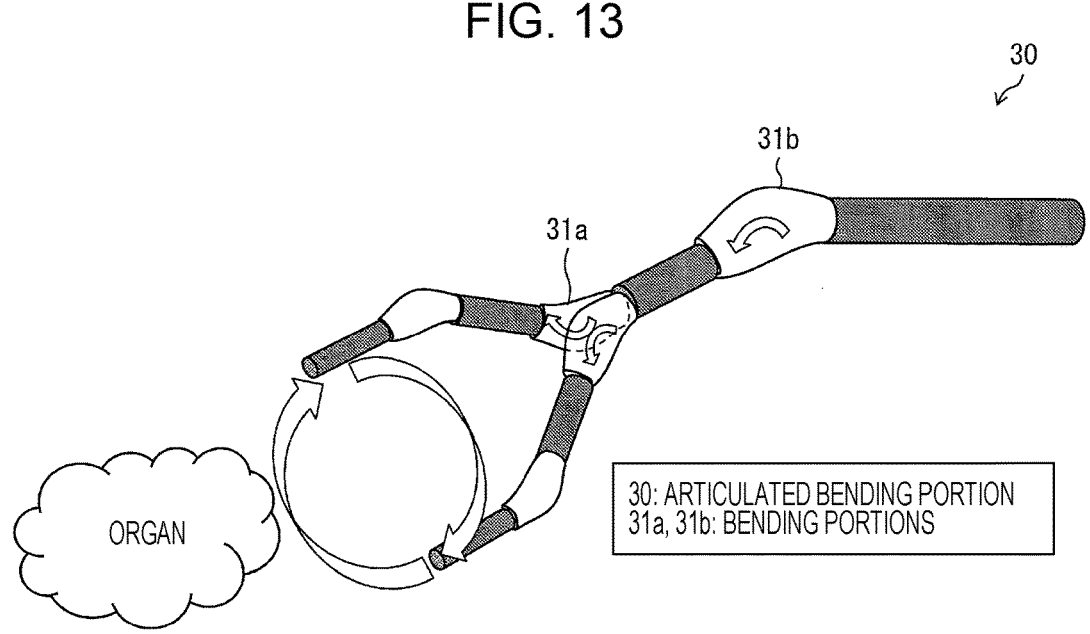
FIG. 13 is a perspective view showing the bending motion of the articulated bending portion according to Embodiment 5 of the present invention.

An application of this structure to the distal end portion, at which a camera is attached, and the middle portion is shown in FIG. 13. An approximate direction of the camera distal end portion is determined by pressurizing the elastic tube 1j to bend the bending portion 31b, and the field of view is moved by bending the bending portion 31a on the side of the distal end portion with the configuration described in Embodiment 2. As the angle of view stays unchanged, non-frustrating movement of the field of view can be achieved.

The above described configuration also reduces the number of elastic tubes to be bundled, so the cross-sectional shape of the articulated bending portion is nearly circular with little unevenness of the surface. This makes the elastic tube 1a easy to wash and sterilize, facilitating its reuse.

Additionally, because the above-described configuration can dispose the non-stretching body 4 and the cable connected with the medical device further inside an elastic tube located within a hollow interior, they can be placed in locations protected by multiple layers of elastic tubes. Thus, if part of the non-stretching body 4 and the cable connected with the medical device is broken for some reason, the broken part is protected by multiple layers of elastic tubes, thus lowering the risk of damage to the human body. For example, if part of the non-stretching body 4 is broken for some reason, the risk of the broken part of the non-stretching body 4 damaging the human body is low even when the non-stretching body 4 has lower stretchability than the elastic tube 1a. As another example, if the cable connected with the medical device is an electric cable, adverse effects such as current leakage due to breakage of the electric cable can be avoided in the human body. Besides, since gas is injected in the elastic tube body 11, should the electric cable is broken, adverse effects of current leakage can be avoided in the elastic tube body 11 because electrical conductivity in the elastic tube body 11 is low.

[Embodiment 6]

Yet another embodiment of the present invention will be described below based on FIGS. 14 to 17. For the sake of description, components having the same functionality as ones described in the previous embodiments are denoted with the same reference numerals and description of such components is omitted.

Embodiment 5 showed an example in which a single elastic tube is used for controlling the middle and proximal end portions and elastic tubes for the distal end portion are disposed in the hollow interior of the elastic tube, while Embodiment 6 shows an example in which four elastic tubes are used for controlling the middle and proximal end portions and an elastic tube for the distal end portion is disposed in the hollow interior of each of the elastic tubes.

(Overview of the Articulated Bending Portion)

Figure 14:
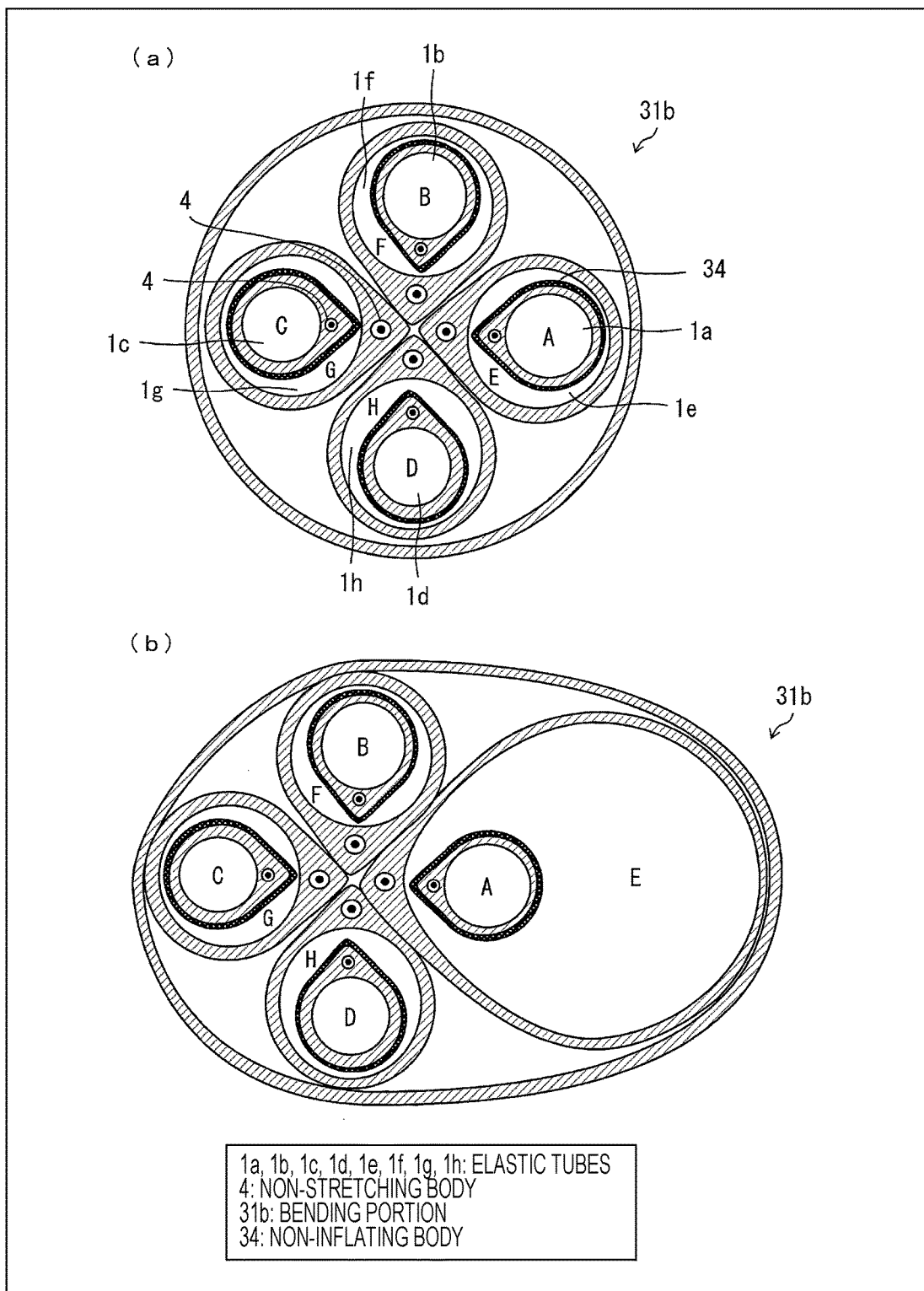
FIGS. 14(a) and 14(b) are cross-sectional views showing an example of the configuration of the middle and proximal end portions of the articulated bending portion according to Embodiment 6 of the present invention.

FIG. 14 shows another variation of the configuration with bending portions using the movable mechanism that operates with one or two bending portions in combination described in Embodiments 1 and 2 for the distal end portion having a camera attached thereon and using four elastic tubes for controlling the middle and proximal end portions.

Detailed description of the configuration of the bending portion 31a on the distal end portion side is omitted as it has been already described in Embodiments 1 and 2.

The cross-sectional structure of the bending portion 31b on the side of the middle and proximal end portions is shown in FIG. 14(a). Elastic tubes 1e to 1h (first elastic tubes) are used for controlling bending in the middle and proximal end portions, and elastic tubes 1a to 1d (second elastic tubes) used in the distal end portion are disposed in the hollow interiors of the elastic tubes 1e to 1h respectively. This configuration reduces burden on the bending motion of the elastic tubes 1e to 1h caused by the elastic tubes 1a to 1d, so bending motions with better controllability can be achieved. The elastic tubes 1a to 1d for use in the distal end portion are structured such that the non-inflating body 34 is wrapped around them.

Further, as to bending of the elastic tubes 1e to 1h, the foregoing description applies: a bending motion is produced by pressurizing and inflating the elastic tubes 1e to 1h. For example, bending in a particular direction can be achieved by pressurizing the elastic tube 1e in the bending portion 31 as shown in FIG. 14(b), or bending in a certain direction can be achieved by changing the position of the elastic tube 1e in another bending portion. In this manner, bending motions such as avoiding a predetermined organ or going behind an organ and viewing it from the back side can be produced based on the positions of the elastic tubes incorporated in advance. Because of a simple structure, there are not many other tubes that can be burden, enabling stable bending motions.

Pressurizing portions may be provided at two or more locations, including a pressurizing portion for pressurizing four tubes A to D that drive bending portions in the distal end portion and a pressurizing portion for pressurizing four tubes E to H that drive the bending portions in middle and proximal end portions.

Figure 15:
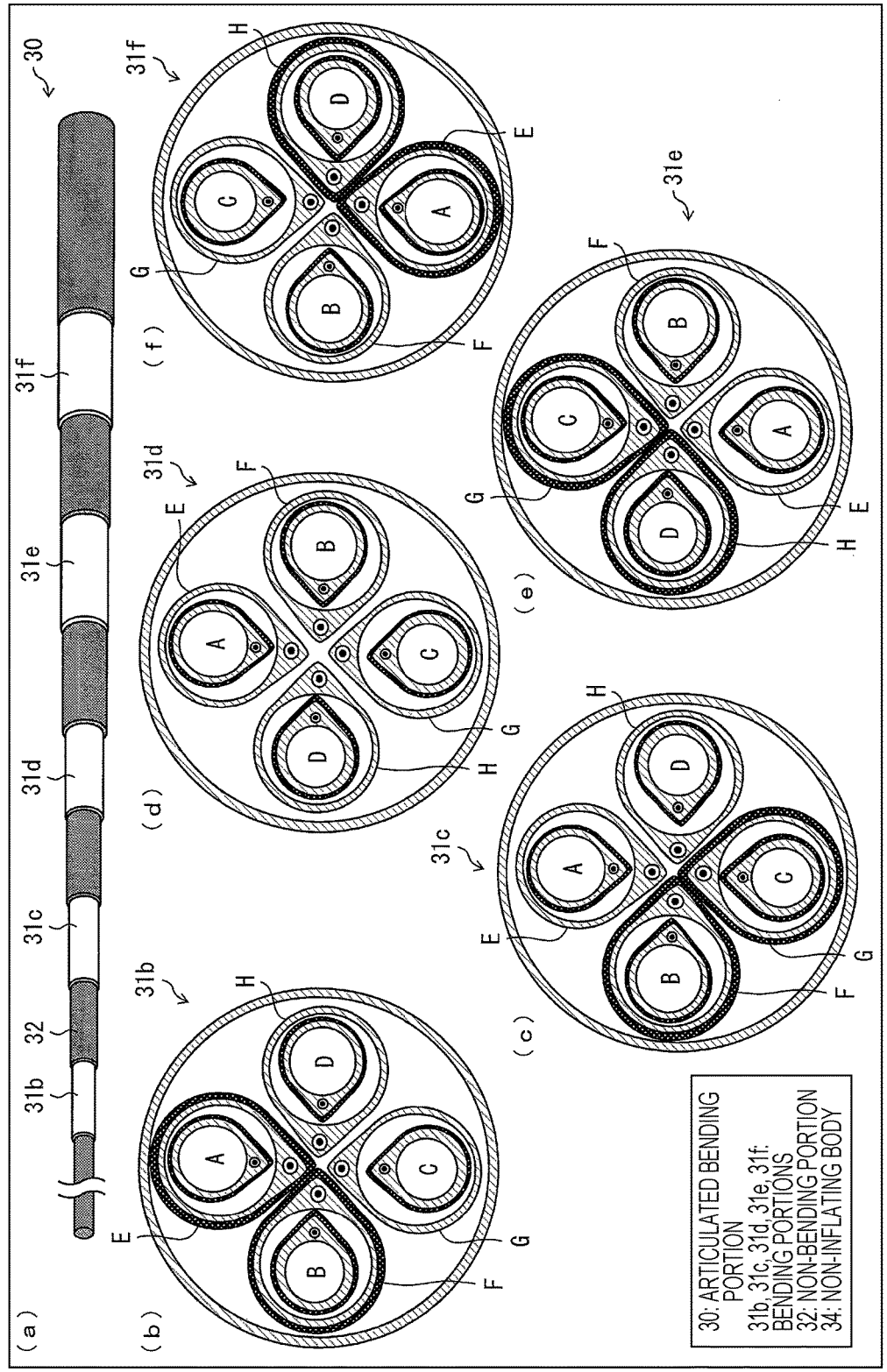
FIGS. 15(a) to 15(f) are perspective and cross-sectional views showing a specific example of the middle and proximal end portions of the articulated bending portion according to Embodiment 6 of the present invention.

A specific example of application of this structure to the middle and proximal end portions is shown in FIG. 15. FIG. 15(a) shows an exemplary configuration that uses four elastic tubes and has five bending portions 31b to 31f. FIG. 15(a) omits illustration of the distal end portion, and only tubes A to D, used in the distal end portion, are shown in the cross-sectional drawings shown in FIGS. 15(b) to 15(f). Detailed description of the configuration of the distal end portion is omitted as it has been already described in Embodiments 1 and 2.

The cross sections of the bending portions are structured as shown in FIGS. 15(b), 15(c), 15(d), 15(e), and 15(f) in order from the side closer to the distal end portion. They will be referred to as a first bending portion 31b, a second bending portion 31c, a third bending portion 31d, a fourth bending portion 31e, and a fifth bending portion 31f in sequence.

As shown in FIG. 15(b), the first bending portion 31b has a structure in which tubes E and F are wrapped with the non-inflating body 34, being configured so as not to inflate, or not bend, when being pressurized.

Similarly, the second bending portion 31c in FIG. 15(c) has a structure in which tubes F and G are wrapped with the non-inflating body 34, the third bending portion 31d in FIG. 15(d) has a structure in which none of the tubes F to H is wrapped with the non-inflating body 34, the fourth bending portion 31e in FIG. 15(e) has a structure in which tubes G and H are wrapped with the non-inflating body 34, and the fifth bending portion 31f in FIG. 15(f) has a structure in which tubes E and H are wrapped with the non-inflating body 34.

In addition, the positions of some of the tubes are interchanged in non-bending portions 32; in the illustrated configuration, none of the tubes are interchanged in the non-bending portion 32 between FIGS. 15(b) and 15(c), whereas tube F and tube H are interchanged in the non-bending portion 32 between FIGS. 15(c) and 15(d), tube E and tube G are interchanged in the non-bending portion 32 between FIGS. 15(d) and 15(e), and tube F and tube H are interchanged again in the non-bending portion 32 between FIGS. 15(e) and 15(f).

Bending motions in the middle and proximal end portions are produced by pressurizing and inflating the tubes E to H. By adopting such a configuration, the position movement feature for avoidance joints shown in FIG. 16 and the interval varying feature for avoidance joints shown FIG. 17 can be provided.

These features will be described in greater detail using drawings. First, FIG. 16(b) shows a bending state during pressurization. As tube E has a structure in which it is wrapped with the non-inflating body 34 in the first and fifth bending portion 31b, 31f, it does not bend when pressurized. Also, because the position of tube E is interchanged in the non-bending portion 32 between the third bending portion 31d and the fourth bending portion 31e, bends in opposite directions occur across that non-bending portion 32. That is, the bending state shown in FIG. 16(b) is assumed.

Bending motions can be produced in the other three tubes with the same principle: the state in FIG. 16(a) occurs when tube H is pressurized, the state in FIG. 16(c) occurs when tube F is pressurized, and the state in FIG. 17(c) occurs when tube G is pressurized.

Next, a case is described where a bend is to be made in a portion closer to the distal end side as shown in FIG. 16(a) from the state of FIG. 16(b). In this case, tube E is gradually depressurized and tube H is gradually pressurized instead. At the same time, the entire tube of the articulated bending portion 30 is rotated by 90 degrees. For the cross-sectional structure in FIG. 15, counterclockwise rotation is gradually applied so that tube H moves to the position of tube E. By doing so, smooth transition from the state of FIG. 16(b) to the state of FIG. 16(a) can be achieved.

Likewise, for a bent to occur on the proximal end side conversely, tube E is gradually depressurized and tube F is gradually pressurized instead, and at the same time, the entire tube is rotated 90 degrees clockwise.

Figure 17:
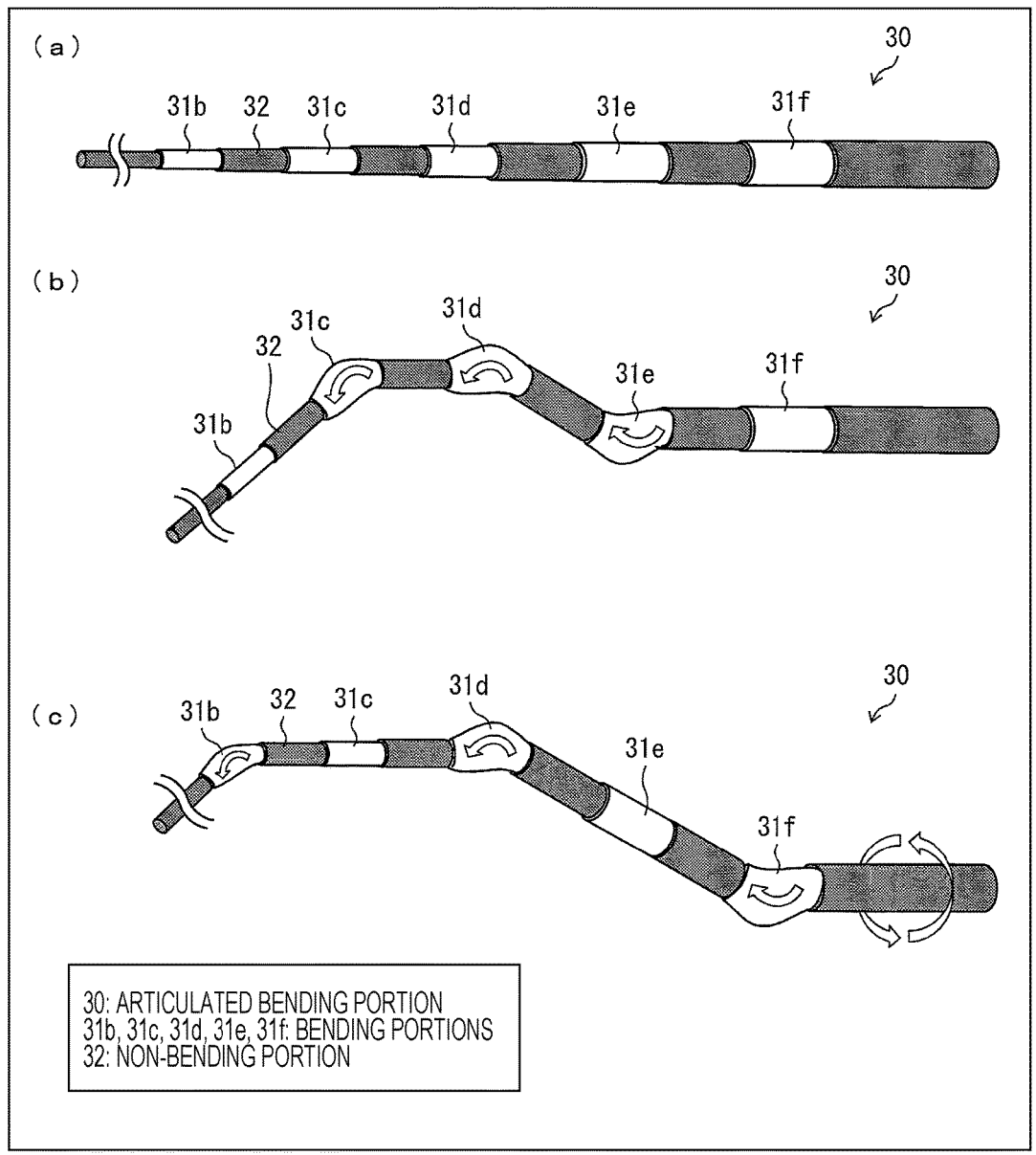
FIG. 17 is a perspective view showing another example of bending motion in the middle and proximal end portions of the articulated bending portion according to Embodiment 6 of the present invention.

As shown in FIG. 17, when the range of joint bending is to be widened from the state of FIG. 17(b) to the state of FIG. 17(c) in order to increase the distance of avoidance, tube E may be gradually depressurized and tube G may be gradually pressurized instead, and at the same time the entire tube may be rotated 180 degrees.

The bending motions shown above are only a few examples and a wide variety of bending motions can be produced by appropriately setting the pressurization states of the four tubes and rotation of the entire tube of the articulated bending portion 30.

Figure 16:
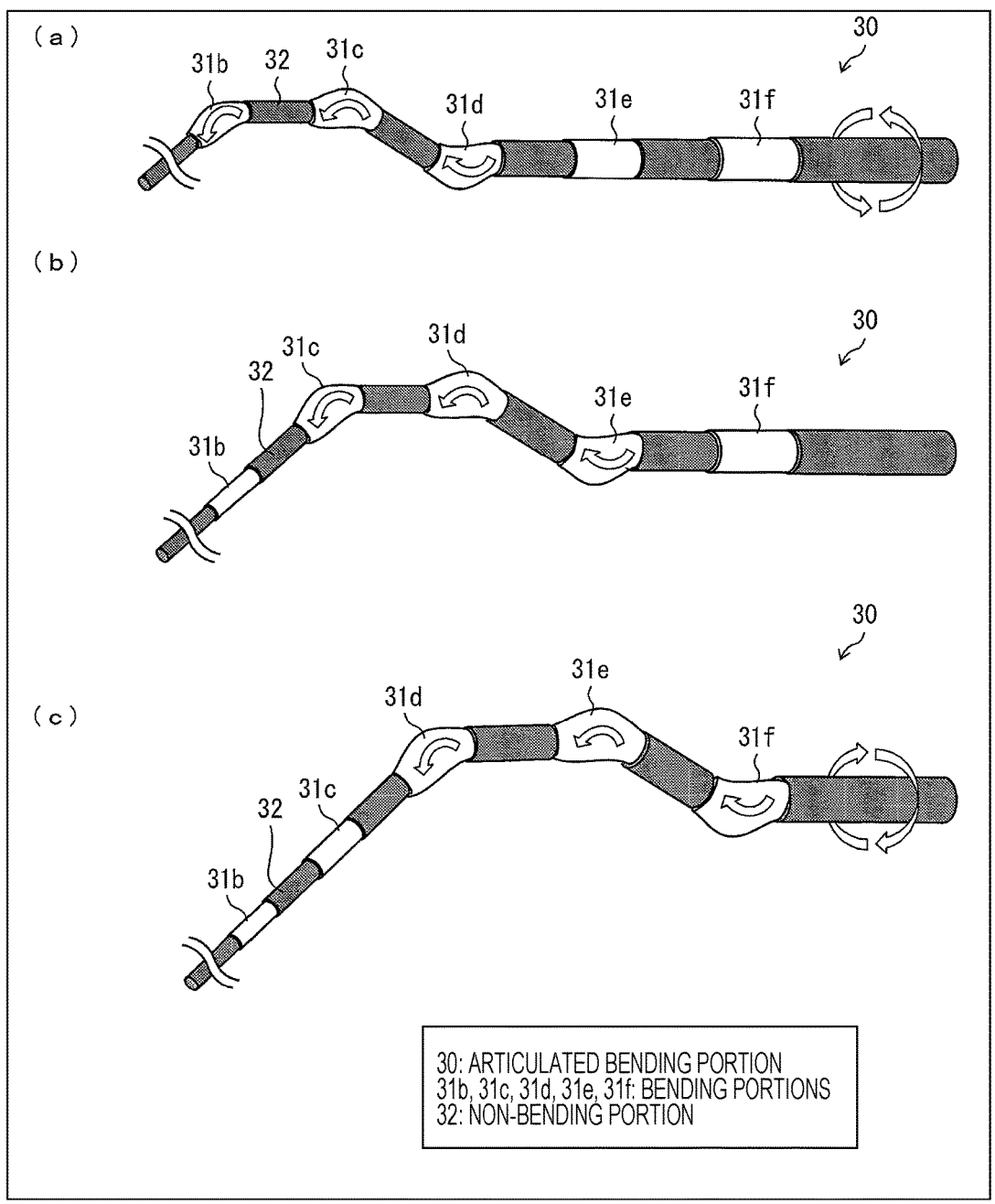
FIG. 16 is a perspective view showing an example of bending motion in the middle and proximal end portions of the articulated bending portion according to Embodiment 6 of the present invention.

In the case of application to an endoscope camera, an approximate position for avoiding an organ is determined with the features described in FIGS. 15 to 17 and then the field of view can be finely adjusted with the camera distal end portion shown in FIG. 13 while an operation is performed so that movement of the field of view non-frustrating for the operator can be achieved.

Such complicated movements can be achieved with a simple structure involving only pressurization of the eight elastic tubes and rotation of the entire tube and a mechanism for attachment and removal, providing an extended range of application to relatively complicated surgeries.

[Embodiment 7]

Yet another embodiment of the present invention will be described below. For the sake of description, components having the same functionality as ones described in the previous embodiments are denoted with the same reference numerals and description of such components is omitted.

(Applications of Medical Devices)

In a case where a catheter as a medical device is attached to the mounting portion at the distal end of the endoscope part 10, a cord for feeding air to the catheter can double as the non-stretching body 4. Air fed to the catheter causes a balloon of the catheter to inflate.

The catheter may be of a guide wire type. In that case, the articulated bending portion 30 is used instead of a guide wire for guiding the direction in which the catheter proceeds. Specifically, the catheter is connected to the non-inflating tube without going through the articulated bending portion 30, and the articulated bending portion 30 (the end opposite to the mounting portion) is connected to the other end of the catheter, that is, on the opposite side of the non-inflating tube. Gas to be contained in the elastic tube 1 within the articulated bending portion 30 is injected from the non-inflating tube through the catheter. Consequently, through adjustment of the pressure of the gas contained in the elastic tube body 11, the articulated bending portion 30 can guide the direction in which the catheter proceeds.

When a laser scalpel as a medical device is attached to the mounting portion, a cord that sends signals for controlling laser emitted by the laser scalpel can double as the non-stretching body 4. The medical device to be attached to the elastic tube 1 may also be an electric scalpel.

(Other Representations of the Present Invention)

The present invention can also be represented as follows.

An endoscope device according to the present invention may be represented as an endoscope device that includes: an articulated bending device consisting of multiple inflatable elastic tubes each of which has a flexible non-stretching body fixed in the length direction in an elastic tube portion, has an elongated hollow cylindrical shape, and is sealed at a distal end portion and contains fluid therein; a camera mounted at the distal end portion of the articulated bending device; non-inflating tubes that are connected to and communicate with the other ends of the elastic tube portions and have a shape of a hollow cylinder in which fluid is contained; a hollow, cylindrical connecting tube connected with the non-inflating tube portion and having flexibility and non-inflatability; and a control unit that controls the fluid pressure in the elastic tubes through the connecting tube and the non-inflating tubes by varying the fluid pressure, in which the control unit controls the fluid pressure in the elastic tubes so that the fluid pressure inflates and deflates the elastic tubes on the opposite side of the non-stretching body, thereby making the articulated bending device curve at a certain angle.

The endoscope device according to the present invention is the endoscope device having the above-described configuration, in which the control unit may be configured to include a piston and a syringe for changing the fluid pressure in the elastic tubes; a fluid pressure sensor for detecting the fluid pressure; a piston driving unit for actuating the piston in the syringe to vary the fluid pressure; a microphone for inputting voice of the operator; and a pressurization control unit to which voice signals input through the microphone and detection signals from the fluid pressure sensor are input and which controls the piston driving unit, and the pressurization control unit may control the piston driving unit based on the voice of the operator to change the fluid pressure in the elastic tubes.

The endoscope device according to the present invention is the endoscope device having the above-described configuration, in which the non-stretching body may be fabricated from polyamide fiber.

The endoscope device according to the present invention is the endoscope device having the above-described configuration, in which the non-stretching body may be an electric cord for supplying electric power to the camera.

[Summarization]

An articulated bending device according to a first aspect of the present invention is for use with a medical instrument (endoscope device 100) and includes: a mounting portion which allows attachment of a medical device (endoscope camera 2, catheter 2a, laser scalpel 2c) at a distal end thereof; an elastic tube body (11) which is sealed at a distal end portion and has an elongated, hollow cylindrical shape; and a fixing portion (13) which can fix a flexible non-stretching body (4) in the long-axis direction of the elastic tube body, characterized in that multiple elastic tubes that enable the elastic tube body (11) to inflate or deflate on the opposite side of the non-stretching body in response to control of the pressure of fluid injected into the elastic tube body are disposed in the hollow interior of the articulated bending device.

The articulated bending device according to the present invention is highly convenient for medical settings as it employs a simple structure easy and inexpensive to manufacture yet is disposable and non-invasive to the human body, being expected to gain wide use in medical settings.

The articulated bending device according to a second aspect of the present invention is the articulated bending device according to the first aspect, in which the fixing portion may fix a non-stretching body formed of a material with lower stretchability than the elastic tube body to the elastic tube body.

With this configuration, a non-stretching body made of a material having lower stretchability than the elastic tube body is fixed to the elastic tube body. For example, if silicone is used for the non-stretching body as the same material as the elastic tubes, the non-stretching body made of silicone material is easy to fix to the elastic tube body. Thus, the non-stretching body of silicone material can be prevented from coming off from the elastic tube if an unexpected shock caused by a contact during a medical procedure occurs to the elastic tube body which has the non-stretching body made of silicone material fixed on it. When polyamide fiber is used for the non-stretching body, for example, polyamide fiber resists fixation to an elastic tube made of silicone material. It would thus be effective for facilitating the removal of the non-stretching body from the elastic tube.

The articulated bending device according to a third aspect of the present invention is the articulated bending device according to the first or second aspect, in which the fixing portion may be disposed between the inner circumferential surface and the outer circumferential surface of the elastic tube body.

With this configuration, the outer circumferential surface of the non-stretching body or a cable connected with a medical device is entirely fixed to the elastic tube body. Accordingly, the curving angle of the elastic tube changes at a constant rate in response to the level of the pressure P of the fluid present in the hollow interior of the elastic tube body. This has the advantage of facilitating the control of the curving angle of the elastic tube body.

The articulated bending device according to a fourth aspect of the present invention is the articulated bending device according to any one of the first to third aspects, in which the positions at which the multiple elastic tubes are disposed in the hollow interior of the articulated bending device may be interchanged in a non-bending portion.

With this configuration, by just pressurizing a single elastic tube, a bending motion in a bending direction determined by the positions of elastic tubes disposed in advance can be achieved in each bending portion independently.

Interchange with the tube on the opposite side in particular enables bends in opposite directions in neighboring two bending portions, so when this configuration is used in the distal end portion, the articulated bending device can be steered without changing the orientation of the distal end portion. This provides a distinctive effect of yielding an image very easy for the operator to see especially when the distal end portion is equipped with a camera because the field of view can be moved without changing the angle of view.

The articulated bending device according to a fifth aspect of the present invention is the articulated bending device according to any one of the first to fourth aspects, in which the elastic tubes for causing a bending motion in the distal end portion of the articulated bending device may be disposed in the hollow interiors of the elastic tubes for operating the middle and proximal end portions.

This configuration reduces burden on the bending motion of the elastic tubes that operate the middle and proximal end portions caused by the elastic tubes that cause a bending motion in the distal end portion, so bending motions with better controllability can be achieved.

This configuration also reduces the number of elastic tubes to be bundled, so the cross-sectional shape of the articulated bending portion is nearly circular with little unevenness of the surface. This makes the elastic tube 1a easy to wash and sterilize, facilitating its reuse.

The articulated bending device according to a sixth aspect of the present invention is the articulated bending device according to any one of the first to fifth aspects, in which the elastic tube body may have a cable connected with the medical device disposed in the hollow interior of the elastic tube body.

With this configuration, because the non-stretching body 4 and the cable connected with the medical device can be positioned further inside an elastic tube disposed within the hollow interior, they can be placed in locations protected by multiple layers of elastic tubes. Thus, if part of the non-stretching body 4 and the cable connected with the medical device is broken for some reason, the broken part is protected by multiple layers of elastic tubes, thus lowering the risk of damage to the human body. For example, if part of the non-stretching body 4 is broken for some reason, the risk of the broken part of the non-stretching body 4 damaging the human body is low even when the non-stretching body 4 has lower stretchability than the elastic tube 1a. As another example, if the cable connected with the medical device is an electric cable, adverse effects such as current leakage caused by breakage of the electric cable can be avoided in the human body. Besides, since gas is injected into the elastic tube body 11, should the electric cable is broken, adverse effects of current leakage can be avoided in the elastic tube body 11 because electrical conductivity in the elastic tube body 11 is low.

Additionally, with this configuration, even in a case where a non-stretching body 4 different from the cable connected with the medical device is fixed to the elastic tube body 11 by the fixing portion 13, the cable connected with the medical device is positioned in the hollow interior of the elastic tube body 11. Thus, the aforementioned adverse effects on the human body that might be caused by the cable connected with the medical device can be avoided. Further, since the portion around the medical device mounted to the elastic tube 1 can be made compact, a cable connected with the medical device will not interfere with a medical procedure.

A control device (20) according to a seventh aspect of the present invention is a control device for controlling the inflation and deflation of the elastic tubes according to in the first aspect, and may include an instruction receiving unit (microphone 25) for receiving an instruction for inflating or deflating the elastic tubes, and a fluid pressure varying unit (piston 21, piston driving unit 24, pressurization control unit 26) for varying the pressure of fluid injected into the hollow interior of the elastic tube body based on the instruction received by the instruction receiving unit.

With this configuration, there is no need for a surgeon (a camera assistant 104) to manipulate the distal end portion of the medical instrument because the distal end portion of the medical instrument is manipulated by the control device; hence, manipulation by such a surgeon (assistant 104) would not interfere with the medical procedure (operation) being conducted by another surgeon (the operator 105). The surgeon (the operator 105) accordingly can concentrate on the medical procedure (operation).

The control device (20) according to an eighth aspect of the present invention is the control device according to the seventh aspect, in which the fluid pressure varying unit may be automatically manipulated based on information acquired by the medical device.

With this configuration, elastic tubes are automatically made to curve through automated manipulation by the fluid pressure varying unit. For example, if an endoscope camera is used as the medical device, an arrangement may be employed in which an image captured by the endoscope camera is displayed on a camera monitor and at the same time the image captured by the endoscope camera is acquired and analyzed by the control device. Then, based on information analyzed by the control device, the fluid pressure varying unit may be automatically manipulated and the pressure of the fluid contained in the elastic tube body can be automatically adjusted so as to automatically change the curving angle of the endoscope camera. The control device has prestored therein image data indicative of the progress of a medical procedure or the like.

The medical device is accordingly steered automatically without the operator conducting the medical procedure giving an instruction for moving the medical device, allowing the operator to concentrate on the medical procedure.

A medical instrument (100) according to a ninth aspect of the present invention may include the elastic tubes described in the first aspect and the control device described in the seventh aspect.

The medical instrument (100) according to a tenth aspect of the present invention is the medical instrument according to the ninth aspect, in which it may be equipped with an endoscope camera (2), a catheter (2a), a laser scalpel (2c), or an electric scalpel as the medical device.

With this configuration, a medical instrument that has both the advantages of the articulated bending device according to the present invention and those of the control device according to the present invention can be provided.

Medical procedures using endoscope cameras, catheters, laser scalpels, and electric scalpels in particular tend to be frequently performed. Thus, the advantages of the present invention can be provided for a wider range of medical settings by equipping the medical instrument according to the present invention with an endoscope camera, a catheter, a laser scalpel, or an electric scalpel as a medical device.

[Summarization of the Embodiments]

A bending device (articulated bending portion 30) according to the first aspect of the present invention is a bending device (articulated bending portion 30) including: a tubular member (elastic tube 1k) having a hollow structure; and a plurality of elastic tubes (1a to 1d) disposed inside the tubular member, characterized in that the elastic tubes each include an elastic tube body (11) which is sealed at a distal end portion and has an elongated, hollow cylindrical shape, and a non-stretching body (4) for suppressing inflation of the elastic tube body; the non-stretching body is fixed to the elastic tube body; a portion of the elastic tube body in which the non-stretching body is fixed is thicker than a remaining portion of the elastic tube body; a portion of the elastic tube body opposite the portion in which the non-stretching body is fixed inflates in a circumferential direction of the elastic tube body in response to increase in an internal pressure, causing the tubular member to bend, and the tubular member includes bending portions that are deformable in response to inflation of the elastic tube body, and non-bending portions that do not deform when the elastic tube body inflates.

With this configuration, since the elastic tube has the non-stretching body, the thick wall portion of the elastic tube body in a part opposite the position where the non-stretching body is disposed inflates in the circumferential direction of the elastic tube body in response to increase in the internal pressure. Thus, bending of the tubular member relative to the amount of inflation is large when compared to a case of uniform inflation of the elastic tube body in the entire circumferential direction. This permits the tubular member to be easily bent without applying large pressure to the elastic tube body. In addition, since the elastic tube is disposed inside the tubular member, inflation of the elastic tube in the circumferential direction (the lateral direction), which do not contribute to bending, is suppressed and inflation of the elastic tube in the long-axis direction (the vertical direction), which directly affects bending of the tubular member can be effectively achieved. Further, since unnecessary inflation in the elastic tube circumferential direction can be suppressed, degradation of elastic tubes caused by mechanical stress that occurs from repeated inflations and deflations can be prevented.

Further, with the configuration above, since the portion of the elastic tube body in which the non-stretching body is fixed is thicker than the remaining portion, the portion in which the non-stretching body is fixed has improved durability and also has increased non-stretchability, leading to such an effect of enabling stable bending motions with no hysteresis generated to pressurization.

The bending device according to the second aspect of the present invention is the bending device according to the first aspect, in which a stretchability of the non-stretching body may be configured to be lower than a stretchability of the elastic tube body.

With this configuration, inflation of the elastic tube body can be suppressed by the non-stretching body.

In the bending device according to the first or second aspect, the non-stretching body may be disposed between the inner circumferential surface and the outer circumferential surface of the elastic tube body.

With such a configuration, no unevenness would occur on the surface (the outer circumferential surface) of the elastic tube body even when the non-stretching body is provided in the elastic tube body. Thus, even when the elastic tubes are exposed on the outermost surface, the elastic tubes are easy to wash and sterilize, facilitating their reuse.

The bending device according to the third aspect of the present invention is the bending device according to the first or second aspect, in which the tubular member may be configured to include bending portions that are deformable in response to inflation of the elastic tube body, and non-bending portions that do not deform when the elastic tube body inflates.

The bending device according to the fourth aspect of the present invention is the bending device according to the third aspect, in which positions of the elastic tubes provided in two bending portions that neighbor one another across the non-bending portion may be configured to be different from each other.

With this configuration, bends in opposite directions can be produced in neighboring two bending portions. By making settings so that the bending angles of the two bending portions are the same, the medical device attached to the distal end portion can be steered without changing the orientation of the distal end portion.

The bending device according to the fifth aspect of the present invention is the bending device according to the third or fourth aspect, and may be configured to include first elastic tubes and second elastic tubes provided inside the first elastic tubes as the elastic tubes, in which the tubular member may include a first bending portion (bending portion 31a) and a second bending portion (bending portion 31b) as the bending portions; in the first bending portion, the first elastic tubes inflate and the second elastic tubes do not inflate in response to increase in their internal pressure; and in the second bending portion, the second elastic tubes inflate and the first elastic tubes do not inflate in response to increase in their internal pressure.

With this configuration, bending of the first bending portion and the second bending portion can be controlled independently from each other.

The bending device according to any one of the first to fifth aspects may be configured such that a cable connected with the medical device is disposed inside the elastic tube body.

In the bending device according to the sixth aspect of the present invention, a bending angle of the tubular member may be configured to change stepwise in response to increase in the internal pressure of the elastic tube body.

With this configuration, the bending motion of the tubular member can be effected with better controllability by controlling the pressure inside the elastic tube body. The bending characteristics of the tubular member can be determined as desired based such as on the design of the elastic modulus of the tubular member and the elastic tubes.

A control device according to the seventh aspect of the present invention is a control device for controlling inflation and deflation of the elastic tube body according to the first aspect, and may be configured to include: an instruction receiving unit for receiving an instruction for inflating or deflating the elastic tubes; and a fluid pressure varying unit for changing a pressure by injecting fluid into a hollow interior of the elastic tube body based on the instruction received by the instruction receiving unit.

The control device according to the seventh aspect may also be configured such that the fluid pressure varying unit is automatically operated based on information acquired by the medical device.

A medical instrument according to the eighth aspect of the present invention may be configured to include the bending device according to the first aspect and the control device according to the seventh aspect.

The medical instrument according to the eighth aspect may be equipped with an endoscope camera, a catheter, a laser scalpel, or an electric scalpel as the medical device.

The present invention is not limited to the embodiments described above but permits various modifications within the scope defined by claims. An embodiment made by combining technical means disclosed in different embodiments appropriately is encompassed in the technical scope of the present invention. Moreover, a novel technical feature can be formed by combining technical means disclosed in different embodiments.

INDUSTRIAL APPLICABILITY

The present invention can be suitably applied to articulated bending devices, control devices, and medical instruments. The present invention is applicable to medical instruments equipped with endoscope cameras, catheters, laser scalpels, and electric scalpels in medical settings in particular.

REFERENCE SIGNS LIST 1 elastic tube
1a to 1k elastic tube
2 endoscope camera
2a catheter
2b balloon
2c laser scalpel
3a to 3d non-inflating tube
4 non-stretching body
5 connecting tube
6 camera monitor
7 flexible stand
8 operating table
10 endoscope part (medical instrument part)
11 elastic tube body
13 fixing portion
14 cable
20 control device
21 piston (air pressure varying unit)
22 syringe
23 air pressure sensor
24 piston driving unit (air pressure varying unit)
25 microphone (instruction receiving unit)
26 pressurization control unit (air pressure varying unit)
30 articulated bending portion (bending device)
31 bending portion (joint)
31a to 31f bending portion (joint)
32 non-bending portion
33 rigid tube
34 non-inflating body
35 pressurizing portion
36 pressurizing valve
37 opening
40 articulated bending device
100 endoscope device (medical instrument)
A, B, C, D, E, F, G, H, I, J tube

The invention claimed is:

1. A bending device comprising: a tubular member having a hollow structure; and a plurality of elastic tubes disposed inside the tubular member, wherein the elastic tubes each include an elastic tube body which is sealed at a distal end portion and has an elongated, hollow cylindrical shape, and a non-stretching body that suppresses inflation of the elastic tube body, the non-stretching body is fixed to the elastic tube body, a portion of the elastic tube body in which the non-stretching body is fixed is thicker than a remaining portion of the elastic tube body, a portion of the elastic tube body opposite the portion in which the non-stretching body is fixed inflates in a circumferential direction of the elastic tube body in response to increase in an internal pressure, causing the tubular member to bend, the tubular member includes bending portions that are deformable in response to inflation of the elastic tube body, and non-bending portions that do not deform when the elastic tube body inflates, and the non-stretching body is embedded in a wall portion between an inner circumferential surface and an outer circumferential surface of the elastic tube body, wherein, in a cross section of each of the elastic tubes, the non-stretching body is provided on a side of the each elastic tube, on which side the elastic tubes are closer to one another.

2. The bending device according to claim 1, wherein a stretchability of the non-stretching body is lower than a stretchability of the elastic tube body.

3. The bending device according to claim 1, wherein positions of the elastic tubes provided in two bending portions that neighbor one another across the non-bending portion are different from each other.

4. The bending device according to claim 1, comprising:
the plurality of elastic tubes include first elastic tubes and second elastic tubes, wherein
the second elastic tubes are provided inside the first elastic tubes,
the tubular member includes a first bending portion and a second bending portion as the bending portions,
in the first bending portion, the first elastic tubes inflate and the second elastic tubes do not inflate in response to increase in the internal pressure, and
in the second bending portion, the second elastic tubes inflate and the first elastic tubes do not inflate in response to increase in the internal pressure.

5. The bending device according to claim 1, wherein a bending angle of the tubular member changes stepwise in response to increase in the internal pressure of the elastic tube body.

6. A control device for controlling inflation and deflation of the elastic tube body according to claim 1, the control device comprising:
a microphone that receives an instruction for inflating or deflating the elastic tubes; and
a pressurization controller that changes a pressure by injecting fluid into a hollow interior of the elastic tube body based on the instruction received by the microphone.

7. A medical instrument comprising:
the bending device according to claim 1; and
a control device including:
a microphone that receives an instruction for inflating or deflating the elastic tubes; and
a pressurization controller that changes a pressure by injecting fluid into a hollow interior of the elastic tube body based on the instruction received by the microphone.

* * * * *